US 8,161,969 B2

(12) United States Patent
Burr et al.

(10) Patent No.: US 8,161,969 B2
(45) Date of Patent: Apr. 24, 2012

(54) DRY POWDER DISPERSING APPARATUS AND METHODS FOR THEIR USE

(75) Inventors: John D. Burr, Redwood City, CA (US); Adrian E. Smith, Emerald Hills, CA (US); Randy K. Hall, Dublin, GA (US); Herm Snyder, Pacifica, CA (US); Carlos A. Schuler, Cupertino, CA (US); George S. Axford, Pacifica, CA (US); Charles Ray, Brentwood, CA (US)

(73) Assignee: Novartis AG, Basel (CH)

( * ) Notice: Subject to any disclaimer, the term of this patent is extended or adjusted under 35 U.S.C. 154(b) by 949 days.

(21) Appl. No.: 12/077,877

(22) Filed: Mar. 21, 2008

(65) Prior Publication Data

US 2008/0230058 A1 Sep. 25, 2008

Related U.S. Application Data

(63) Continuation of application No. 11/076,418, filed on Mar. 9, 2005, now Pat. No. 7,422,013, which is a continuation of application No. 10/327,633, filed on Dec. 19, 2002, now Pat. No. 6,901,929, which is a continuation of application No. 09/873,946, filed on Jun. 4, 2001, now Pat. No. 6,546,929, which is a continuation of application No. 09/312,434, filed on May 14, 1999, now Pat. No. 6,257,233.

(60) Provisional application No. 60/087,929, filed on Jun. 4, 1998.

(51) Int. Cl.
*A61M 15/00* (2006.01)
*A61M 16/00* (2006.01)
(52) U.S. Cl. .......... 128/203.21; 128/203.15; 128/203.12
(58) Field of Classification Search ............. 128/203.21, 128/203.15, 203.24, 203.23, 200.23, 200.24, 128/202.22, 203.12
See application file for complete search history.

(56) References Cited

U.S. PATENT DOCUMENTS 513,189 A 1/1894 Knode
(Continued)

FOREIGN PATENT DOCUMENTS

CA 2064860 3/2002
(Continued)

OTHER PUBLICATIONS

Bohnet Matthias "Calculation and Design of Gas/Solid-Injectors" Powder Technol p. 302-313 (1984).
(Continued)

*Primary Examiner* — Justine Yu
*Assistant Examiner* — Colin W Stuart
(74) *Attorney, Agent, or Firm* — Zilka-Kotab, PC

(57) ABSTRACT

The invention provides various apparatus and methods for aerosolizing a powdered medicament. In one exemplary embodiment, an apparatus includes a pressurization cylinder, and a piston which is slidable within the cylinder to pressurize a gas. A handle is coupled to the piston and is movable between an extended position and a home position to pressurize the gas. An aerosolizing mechanism is included and is configured to aerosolize a powdered medicament that is held within a receptacle with pressurized gas from the cylinder. A carriage assembly is included to receive the receptacle and to couple the receptacle to the aerosolizing mechanism. A first and a second interlock are operably engageable with the carriage assembly to prevent coupling of the receptacle with the aerosolization mechanism. The first interlock is released to allow movement of the carriage upon movement of the handle to the extended position. The second interlock remains engaged if the receptacle is only partially inserted into the carriage assembly.

19 Claims, 35 Drawing Sheets

U.S. PATENT DOCUMENTS

| | | | |
|---|---|---|---|
| 2,533,065 A | 12/1950 | Taplin et al. |
| 2,549,303 A | 4/1951 | Friden |
| 2,570,774 A | 10/1951 | Davis |
| 2,598,525 A | 5/1952 | Fox |
| 2,603,216 A | 7/1952 | Taplin |
| 3,362,405 A | 1/1968 | Hazel |
| 3,425,600 A | 2/1969 | Abplanalp |
| 3,812,854 A | 5/1974 | Michaels et al. |
| 3,906,950 A | 9/1975 | Cocozza |
| 3,918,451 A | 11/1975 | Steil |
| 3,921,637 A | 11/1975 | Bennie et al. |
| 3,964,483 A | 6/1976 | Mathes |
| 3,967,761 A | 7/1976 | Melton, Jr. et al. |
| 3,991,304 A | 11/1976 | Hillsman |
| 3,991,761 A | 11/1976 | Cocozza |
| 3,994,421 A | 11/1976 | Hansen |
| 4,018,185 A | 4/1977 | Myers |
| 4,036,223 A | 7/1977 | Obert |
| 4,046,146 A | 9/1977 | Rosskamp et al. |
| 4,069,819 A | 1/1978 | Valentini |
| 4,098,273 A | 7/1978 | Glenn |
| 4,105,027 A | 8/1978 | Lundquist |
| 4,114,615 A | 9/1978 | Wetterlin |
| 4,249,526 A | 2/1981 | Dean et al. |
| 4,253,468 A | 3/1981 | Lehmbeck |
| 4,338,931 A | 7/1982 | Cavazza |
| 4,446,862 A | 5/1984 | Baum et al. |
| 4,452,239 A | 6/1984 | Malem |
| 4,484,577 A | 11/1984 | Sackner et al. |
| 4,534,343 A | 8/1985 | Nowacki et al. |
| 4,558,710 A | 12/1985 | Eichler |
| 4,570,630 A | 2/1986 | Elliott et al. |
| 4,624,251 A | 11/1986 | Miller |
| 4,627,432 A | 12/1986 | Newell et al. |
| 4,649,911 A | 3/1987 | Knight et al. |
| 4,668,218 A | 5/1987 | Virtanen |
| 4,677,975 A | 7/1987 | Edgar et al. |
| 4,739,754 A | 4/1988 | Shaner |
| 4,778,054 A | 10/1988 | Newell et al. |
| 4,790,305 A | 12/1988 | Zoltan et al. |
| 4,807,814 A | 2/1989 | Douche et al. |
| 4,811,731 A | 3/1989 | Newell et al. |
| 4,819,629 A | 4/1989 | Jonson |
| 4,823,784 A | 4/1989 | Bordoni et al. |
| 4,852,561 A | 8/1989 | Sperry |
| 4,860,740 A | 8/1989 | Kirk et al. |
| 4,884,565 A | 12/1989 | Cocozza |
| 4,889,114 A | 12/1989 | Kladders |
| 4,907,583 A | 3/1990 | Wetterlin et al. |
| 4,926,852 A | 5/1990 | Zoltan et al. |
| 4,942,544 A | 7/1990 | McIntosh et al. |
| 4,984,158 A | 1/1991 | Hillsman |
| 4,986,269 A | 1/1991 | Hakkinen |
| 4,995,385 A | 2/1991 | Valentini et al. |
| 5,020,527 A | 6/1991 | Dessertine |
| 5,027,806 A | 7/1991 | Zoltan et al. |
| 5,033,463 A | 7/1991 | Cocozza |
| 5,035,237 A | 7/1991 | Newell et al. |
| 5,048,514 A | 9/1991 | Ramella |
| 5,099,833 A | 3/1992 | Michaels |
| 5,113,855 A | 5/1992 | Newhouse |
| 5,161,524 A | 11/1992 | Evans |
| 5,186,164 A | 2/1993 | Raghuprasad |
| 5,186,166 A | 2/1993 | Riggs et al. |
| 5,201,308 A | 4/1993 | Newhouse |
| 5,207,217 A | 5/1993 | Cocozza et al. |
| 5,284,133 A | 2/1994 | Burns et al. |
| 5,287,850 A | 2/1994 | Haber et al. |
| 5,295,479 A | 3/1994 | Lankinen |
| 5,309,900 A | 5/1994 | Knoch et al. |
| 5,320,714 A | 6/1994 | Brendel |
| 5,331,953 A | 7/1994 | Andersson et al. |
| 5,337,740 A | 8/1994 | Armstrong et al. |
| 5,349,947 A | 9/1994 | Newhouse et al. |
| 5,355,872 A | 10/1994 | Riggs et al. |
| 5,363,842 A | 11/1994 | Mishelevich et al. |
| 5,366,122 A | 11/1994 | Guentert et al. |
| 5,388,572 A | 2/1995 | Mulhausser et al. |
| 5,392,961 A * | 2/1995 | Starrett .................. 222/153.14 |
| 5,404,871 A | 4/1995 | Goodman et al. |
| 5,458,135 A | 10/1995 | Patton et al. |
| 5,480,386 A | 1/1996 | Brohy et al. |
| 5,505,194 A | 4/1996 | Adjei et al. |
| 5,533,502 A | 7/1996 | Piper |
| 5,568,884 A | 10/1996 | Bruna |
| 5,596,982 A | 1/1997 | Blaha-Schnabel |
| 5,645,050 A | 7/1997 | Zierenberg et al. |
| 5,645,051 A * | 7/1997 | Schultz et al. ........... 128/203.15 |
| 5,694,920 A | 12/1997 | Abrams et al. |
| 5,740,794 A | 4/1998 | Smith et al. |
| 5,755,221 A | 5/1998 | Bisgaard |
| 5,775,320 A | 7/1998 | Patton et al. |
| 5,785,049 A | 7/1998 | Smith et al. |
| 5,797,391 A * | 8/1998 | Cook et al. ............... 128/203.15 |
| 5,840,279 A | 11/1998 | Narodylo et al. |
| 6,006,747 A | 12/1999 | Eisele et al. |
| 6,029,661 A | 2/2000 | Whaley et al. |
| 6,029,663 A * | 2/2000 | Eisele et al. ............. 128/203.21 |
| 6,089,228 A | 7/2000 | Smith et al. |
| 6,116,237 A | 9/2000 | Schultz et al. |
| 6,119,688 A | 9/2000 | Whaley et al. |
| 6,123,070 A | 9/2000 | Bruna et al. |
| 6,138,668 A | 10/2000 | Patton et al. |
| 6,179,164 B1 | 1/2001 | Fuchs |
| 6,257,233 B1 | 7/2001 | Burr et al. |
| 6,367,473 B1 | 4/2002 | Kafer |
| 6,401,712 B1 | 6/2002 | von Schuckmann |
| 6,484,715 B1 | 11/2002 | Ritsche et al. |
| 6,520,179 B1 | 2/2003 | von Schuckmann et al. |
| 6,546,929 B2 | 4/2003 | Burr et al. |
| 7,422,013 B2 * | 9/2008 | Burr et al. ................ 128/200.23 |

FOREIGN PATENT DOCUMENTS

| | | |
|---|---|---|
| DE | 471490 | 8/1931 |
| DE | 1147354 | 4/1963 |
| DE | 19704849 | 2/1997 |
| DE | 19704849 | 8/1998 |
| EP | 0094231 | 11/1983 |
| EP | 0129985 | 1/1985 |
| EP | 0387222 | 9/1990 |
| EP | 0237507 | 12/1991 |
| EP | 0467172 | 1/1992 |
| EP | 0468914 | 1/1992 |
| EP | 0473965 | 3/1992 |
| EP | 0490797 | 6/1992 |
| EP | 0506293 | 9/1992 |
| EP | 0412648 | 6/1993 |
| EP | 0347779 | 5/1994 |
| EP | 0525720 | 12/1996 |
| FR | 2257351 | 8/1975 |
| FR | 2700279 | 7/1994 |
| GB | 636854 | 5/1950 |
| GB | 2063075 | 6/1981 |
| GB | 2164569 | 3/1986 |
| GB | 2230456 | 10/1990 |
| NL | 79234 | 5/1955 |
| NL | 7712041 | 5/1979 |
| SU | 628930 | 10/1978 |
| SU | 1003926 | 3/1983 |
| WO | WO 8704354 | 7/1987 |
| WO | WO 8907464 | 8/1989 |
| WO | WO 9007351 | 7/1990 |
| WO | WO 9015635 | 12/1990 |
| WO | WO 9102558 | 3/1991 |
| WO | WO 9210229 | 6/1992 |
| WO | WO 9220391 | 11/1992 |
| WO | WO 9300951 | 1/1993 |
| WO | WO 9309832 | 5/1993 |
| WO | WO 9403225 | 2/1994 |
| WO | WO 94/06491 | 3/1994 |
| WO | WO 9406498 | 3/1994 |
| WO | WO 9408552 | 4/1994 |
| WO | WO 9411044 | 5/1994 |
| WO | WO 9506491 | 3/1995 |
| WO | WO 9609085 | 3/1996 |
| WO | WO 9619253 | 6/1996 |

OTHER PUBLICATIONS

Budrick GK et al "Ejector Feeders for Pneumatic Transport Systems" Translated from Khim Neft Mashinostr 9:44-46 (1978).

Byron Peter R et al "Drug Delivery via the Respiratory Tract" J Aerosol Med 7(1):49-75 (1994).

Elliott RB et al "Parenteral Absorption of Insulin from the Lung in Diabetic Children" Aust Paediatr J 23:293-297 (1987).

Fox Lawrence S et al "Performance of a venturi educator as a feeder in a pneumatic conveying system" Powder Bulk Eng p. 33-36 (1988).

Pittman an et al "Pneumatic Conveying of Bulk Solids Using a Vacuum Aerated Feed Nozzle" J Powder Bulk Solids Technol 11(1):1-6 (1978).

Witham Clyde L et al "Dry Dispersion with Sonic Velocity Nozzles" Workshop on Dissemination Techniques for Smoke and Obscurants, Chem Sys Lab, Aberdeen Proving Ground, MD (Mar. 14-16, 1983).

Zholob VM et al "Effect of Injector Unit Design on the Particle Size of Atomized Powder" Translated from Poroshk Metall 6(198):13-16 (1979).

"Ejectors" Chemical Engineers' Handbook, $5^{th}$ Ed, Robert H Perry Ed, McGraw-Hill Book Co, 6-29-6-32.

Bibliographic data of AU 5328890 (Oct. 18, 1990).

English description of DE 471490.

English translation of AU 2038492, abstract (Feb. 4, 1993).

English translation of AU 6008490, abstract (Feb. 7, 1991).

English translation of DE 19704849, abstract (Aug. 13, 1998).

English translation of EP 0473965, abstract (Mar. 11, 1992).

English translation of FR 2700279, abstract (Jul. 13, 1994).

\* cited by examiner

DRY POWDER DISPERSING APPARATUS AND METHODS FOR THEIR USE

CROSS-REFERENCES TO RELATED APPLICATIONS

This application is a continuation of U.S. patent application Ser. No. 11/076,418, which is a continuation of U.S. patent application Ser. No. 10/327,633, filed Dec. 19, 2002, now U.S. Pat. No. 6,901,929, which is a continuation of U.S. patent application Ser. No. 09/873,946, filed Jun. 4, 2001, now U.S. Pat. No. 6,546,929, which is a continuation of U.S. patent application Ser. No. 09/312,434, filed May 14, 1999, now U.S. Pat. No. 6,257,233, and claims the benefit of U.S. Provisional Patent Application Ser. No. 60/087,929, filed Jun. 4, 1998, the complete disclosure of which is herein incorporated by reference.

BACKGROUND OF THE INVENTION

The invention relates generally to the field of pulmonary drug delivery. More specifically, the invention relates to dry powder dispersion devices and methods for dispersing dry powder medicaments for inhalation by a patient.

Pulmonary drug delivery is becoming a promising way to deliver drugs to a patient. Pulmonary drug delivery relies on inhalation of a drug dispersion or an aerosol by the patient so that the active drug within the dispersion can reach the distal (alveolar) regions of the lung. It has been found that certain drugs are readily absorbed through the alveolar regions directly into blood circulation. For example, pulmonary delivery is particularly promising for the delivery of proteins and polypeptides which are difficult to deliver by other routes of administration. Such pulmonary delivery is effective both for systemic delivery and for localized delivery to treat diseases of the lungs.

A variety of approaches have been proposed to achieve pulmonary drug delivery. Such approaches include the use of liquid nebulizers, metered dose inhalers (MDI's) and dry powder dispersion devices. Of these approaches, dry powder dispersion devices are of particular interest. Exemplary embodiments of such dry powder dispersion devices are described in U.S. Pat. No. 5,740,794 and Ser. No. 08/309,691, filed Sep. 21, 1994, the complete disclosures of which are herein incorporated by reference. These patents describe hand-held powder dispersion devices which extract powder from a receptacle and aerosolize the powder so that the aerosolized powder may be inhaled by a patient. Such dry powder dispersion devices have proven to be tremendously successful in adequately aerosolizing dry powders for subsequent inhalation.

Even so, it would be desirable to provide various enhancements to increase the marketability, ease of use, functionality, and other features of such dry powder dispersion devices. Hence, it is an object of the invention to provide improved dry powder dispersion devices and methods for their use.

SUMMARY OF THE INVENTION

The invention provides exemplary systems, apparatus and methods for aerosolizing a powdered medicament. One exemplary apparatus of the invention comprises a pressurization cylinder and a piston that is slidable within the cylinder to pressurize a gas within the cylinder. A handle is coupled to the cylinder and is movable between an extended position and a home or retracted position to pressurize the gas within the cylinder. An aerosolizing mechanism is further provided to aerosolize a powdered medicament that is held within a receptacle using pressurized gas from the cylinder. A carriage assembly is provided to receive the receptacle and to couple the receptacle to the aerosolizing mechanism so that the powder may be extracted from the receptacle and aerosolized. The apparatus further includes a first and a second interlock which may be operated to engage the carriage assembly, thereby preventing coupling of the receptacle with the aerosolizing mechanism. The first interlock is released to allow movement of the carriage when the handle is moved to the fully extended position. The second interlock becomes engaged with the carriage when the receptacle is only partially inserted into the carriage assembly.

With such a configuration, the apparatus is operated to aerosolize the powdered medicament by inserting the receptacle into the carriage assembly to a fully loaded position to ensure that the second interlock is not engaged with the carriage assembly. The handle is then extended to a fully extended position and retracted back to the home position to produce a charge of pressurized gas and to release the first interlock from the carriage assembly. A fire button on the apparatus is then operated to move the carriage assembly toward the aerosolizing mechanism until the receptacle is coupled with the aerosolizing mechanism. Upon coupling of the aerosolizing mechanism, the charge of pressurized gas is released to aerosolize the powdered medicament that is held within the receptacle.

Such a configuration is advantageous in that the aerosolizing apparatus may not be operated if the receptacle is not fully inserted and the handle is not fully extended. In this way, controls are provided to ensure correct operation of the aerosolization apparatus.

In one particularly preferable aspect, the receptacle has a front end, a back end, and a cavity which holds the medicament. The front end includes at least one notch, and the carriage assembly includes a key so that the receptacle may not be fully inserted into the carriage assembly if the notch does not mate with the key. In this way, the carriage assembly may not be operated to couple the receptacle with the aerosolizing, mechanism if the notch does not mate with the key, thereby preventing full insertion of the receptacle into the carriage assembly.

In one particular aspect, the aerosolization apparatus further includes a sensor arm having a roller. The roller rolls over the cavity during insertion of the receptacle into the carriage assembly to move the sensor arm against the second interlock, thereby causing a latch on the second interlock to engage the carriage assembly until the roller rolls over the entire cavity. In this way, the latch will remain engaged with the carriage assembly to prevent its movement as long as the roller is in apposition to the cavity. Once fully inserted, the latch is released to allow operation of the carriage assembly. In still a further aspect, the sensor arm defines a well which receives the cavity when the receptacle is fully inserted. The well aligns the cavity with the aerosolizing mechanism to facilitate coupling of the receptacle to the aerosolizing mechanism.

In one particular aspect, the apparatus further includes a catch which engages the carriage assembly when the carriage assembly is moved to couple the receptacle to the aerosolizing mechanism. A release button is provided to release the carriage assembly from the catch. In this way, the carriage assembly will not accidentally be lowered to decouple the receptacle from the aerosolizing mechanism until the powdered medicament has been aerosolized. In another aspect, a valve is disposed in an airway between the cylinder and the aerosolizing mechanism. The valve has an open position and a closed position, and is generally in the closed (but unlocked)

position during extension of the handle to the extended position. Such a configuration is advantageous in that the air employed to fill the cylinder is not drawn through the airway, thereby providing a cleaner supply of air to fill the cylinder.

In one particular embodiment, an aerosolizing apparatus is provided which comprises a housing, a pressurization cylinder, and a piston that is slidable within the cylinder to pressurize a gas within the cylinder. The piston is pivotally attached to the housing, and a handle is operably attached to both the housing and cylinder. The handle is operated to move the cylinder relative to the piston to pressurize a gas within the cylinder. An aerosolization mechanism is provided to receive gas from the cylinder to aerosolize a powdered medicament. Construction of the apparatus in this manner is advantageous in that the piston may pivot relative to the housing as the handle is operated. In this way, the piston remains generally aligned with the cylinder during operation of the handle, thereby facilitating operation of the handle and reducing wear between the components.

In one particular aspect, a linkage is disposed between the handle and the cylinder. The linkage is pivotally attached to the housing and the cylinder to further facilitate operation of the handle. In another aspect, the housing includes a top end and a bottom end, and the aerosolizing mechanism is disposed near the top end. Further, the piston is pivotally attached to the housing at the bottom end. Such a configuration is advantageous when a one-way check valve is disposed in the piston because the check valve will be disposed near the bottom end of the housing to reduce the chances of having any powder which may fall through the housing from accumulating on the check valve.

In a further embodiment, the invention provides an aerosolizing device which comprises a housing and a capture chamber which extends from the housing. An aerosolizing mechanism is disposed in the housing to introduce a powdered medicament into the capture chamber. The aerosolizing mechanism is provided with air channels which allow air to enter into the capture chamber when a patient inhales to extract the powdered medicament from the capture chamber. The aerosolizing mechanism further includes a structure to distribute air entering into the capture chamber through the air channels such that the powdered medicament is removed from the capture chamber as a bolus that is substantially unmixed with the entering air.

Such a device is operated by dispersing the powdered medicament into the capture chamber and then inhaling from the capture chamber to extract the powdered medicament. Air is allowed to enter into the capture chamber through the air channels in a manner such that substantially none of the incoming air mixes with the powdered medicament to allow the medicament to be removed as a bolus. Hence, by introducing the air in this manner, the air serves as a piston to uniformly lift the aerosolized powder up through the capture chamber where it is inhaled by the patient.

In one particular aspect, the capture chamber has a geometric center and the aerosolizing mechanism is offset from the center because of the inclusion of other component parts within the housing. The structure is fashioned to distribute more air to regions of the capture chamber which are more remote from the geometric center. In this way, the remotest regions of the capture chamber will receive more air so that substantially no mixing of the powdered medicament occurs as air is drawn into the capture chamber during inhalation by the patient. In another aspect, the structure comprises a curved flange member and serves to channel some of the air radially outward as it enters into the capture chamber.

In one particularly preferable aspect, the aerosolizing mechanism includes a cylindrical passage or channel through which the powdered medicament passes to reach the capture chamber. The top end of the housing is generally perpendicular to a distal end of the passage. In this way, as the powdered medicament enters into the capture chamber, it will tend to disperse evenly throughout the capture chamber. In yet another aspect, a flexible seal is coupled to the housing to provide a seal with the capture chamber. The flexible nature of the seal is advantageous in that the capture chamber may easily be slid over the housing without causing excessive wear to the seal.

In one particular embodiment, the invention provides a device for aerosolizing a powdered medicament which comprises a housing having at least one piercing element for piercing a hole in a receptacle that contains a powdered medicament. A core is insertable into the housing and has an extraction lumen or tube and at least one air channel. The air channel is aligned with the piercing element when the core is inserted into the housing to allow air to flow into the receptacle through the air channel. A source of pressurized gas is further provided to extract the powdered medicament through the extraction lumen when the extraction lumen is inserted into the receptacle. Use of the housing and core is advantageous in that the core may be manufactured with a relatively small cost and may be made disposable, while the housing which includes the piercing element may be re-used.

DESCRIPTION OF THE SPECIFIC EMBODIMENTS

Figure 1:
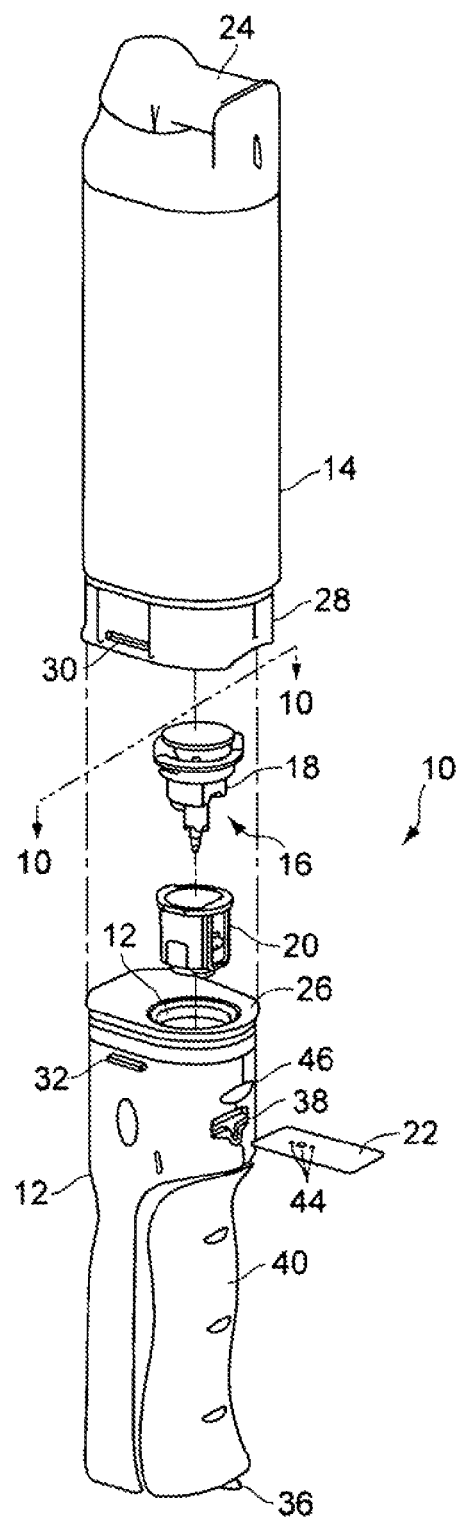
FIG. 1 is an exploded front perspective view of an exemplary apparatus for aerosolizing a powdered medicament according to the invention.
Figure 2:
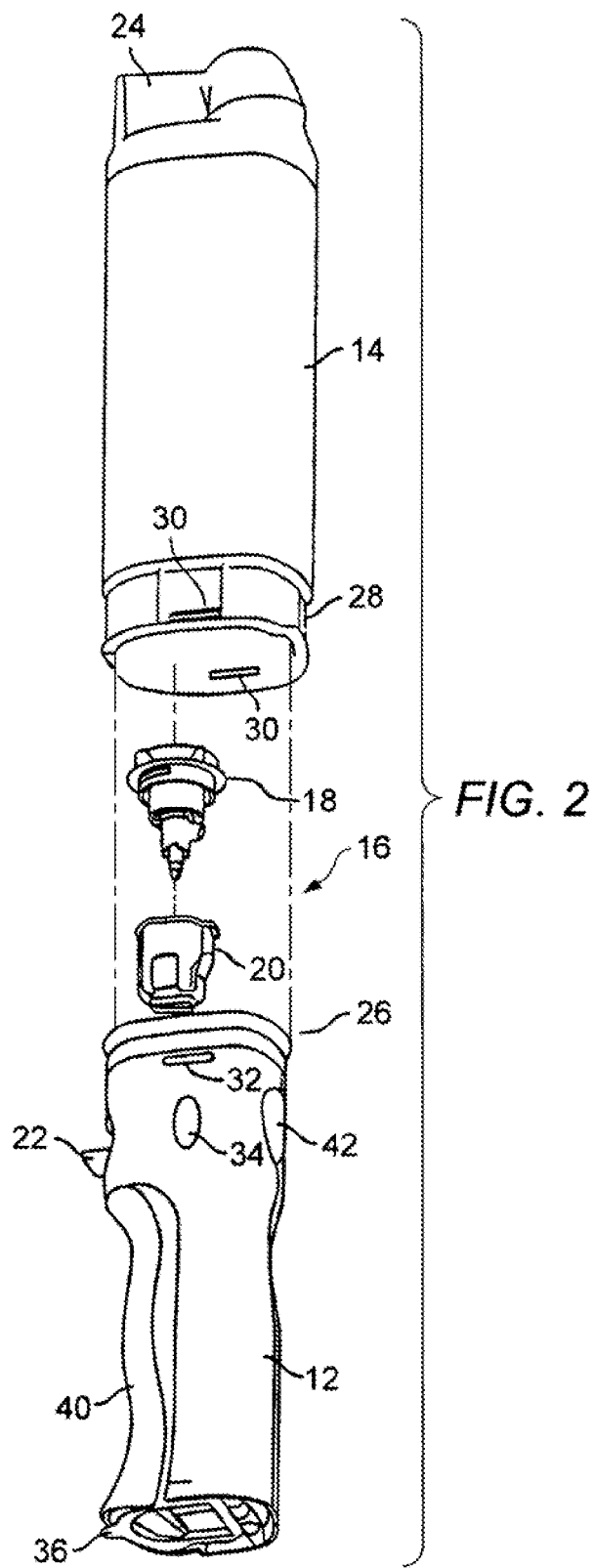
FIG. 2 is a rear perspective view of the apparatus of FIG. 1.

Referring now to FIGS. 1 and 2, an exemplary embodiment of an apparatus 10 for aerosolizing a powdered medicament will be described. Apparatus 10 comprises a base unit 12 and a capture chamber 14 which is removably attachable to base unit 12. Capture chamber 14 is configured to slide over base unit 12 to reduce the overall size of apparatus 10 during storage and to protect the components within base unit 12. Shown exploded from base unit 12 is an aerosolization mechanism 16 which comprises a core 18 and a housing 20. Base unit 12 includes an opening 21 to receive aerosolization mechanism 16. Base unit 12 is configured to receive a receptacle 22 which holds a powdered medicament. Apparatus 10 is operated to couple aerosolization mechanism 16 with receptacle 22, and then to extract the powdered medicament from receptacle 22. The extracted powder is then deagglomerated and dispersed and delivered into capture chamber 14 where it will be available for inhalation by a patient.

Capture chamber 14 includes a mouthpiece 24 that is rotatable between an open position and a closed position. During aerosolization, mouthpiece 24 is in the closed position as shown in FIGS. 1 and 2. When the patient is ready to inhale the aerosolized medicament, mouthpiece 24 is rotated 180 degrees to the open position where the patient may place his mouth over the mouthpiece and inhale the powdered medicament from capture chamber 14.

Figure 2A:
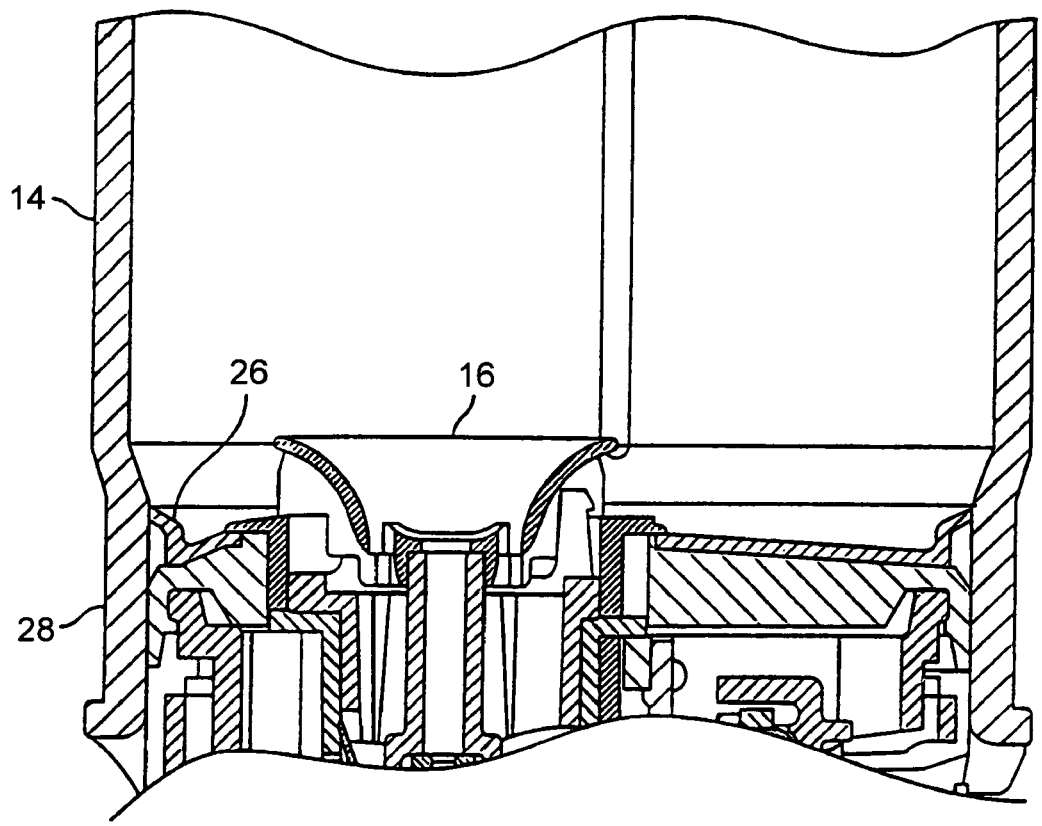
FIG. 2A is a cross-sectional side view of a seal for engaging a necked region of the capture chamber of the apparatus of FIG. 1 according to the invention.

As previously mentioned, capture chamber 14 is slidable over base unit 12 to reduce the size of apparatus 10 during storage and to protect the components of base unit 12. Base unit 12 includes a seal 26 which extends radially outward from base unit 12 and engages the walls of capture chamber 14 so that a seal is provided between base unit 12 and capture chamber 14. As best shown in FIG. 2A, capture chamber 14 includes a necked region 28 which comes into contact with seal 26 as capture chamber 14 is moved to a fully extended position. Seal 26 is preferably constructed of a rubber using a two-shot molding process to attach seal 26 to base unit 12. Use of necked region 28 is particularly advantageous in that seal 26 disengages from capture chamber 14 as capture chamber 14 is slid over base unit 12 to a closed or storage position. In this way, wear of seal 26 is significantly reduced.

Referring back to FIGS. 1 and 2, necked region 28 further includes a pair of apertures 30 into which a pair of latches 32 on base unit 12 are received when capture chamber 14 is moved to the extended position. Upon reaching the extended position, the latches, which are spring-biased, slide into apertures 30 to prevent capture chamber 14 from being pulled from base unit 12. Further, engagement of latches 32 with apertures 30 maintain the capture chamber 14 in the extended position so that it will not accidentally slide back over base unit 12. To disengage latches 32 from apertures 30, a chamber release button 34 is depressed. Upon depression of chamber release button 34, latches 32 are moved back into base unit 12 where capture chamber 14 may be removed from base unit 12 or slid back over base unit 12 to the storage position.

Conveniently, base unit 12 includes a pull ring 36 which may be grasped with a finger of one hand while capture chamber 14 is grasped with the other hand to facilitate movement of capture chamber 14 from the storage position to the extended position. Pull ring 36 is attached to base unit 12 by a spring-loaded hinge mechanism so that pull ring 36 will return to a flush position with base unit 12 when not in use.

Apparatus 10 is operated by inserting receptacle 22 into a carriage assembly 38 of base unit 12. Optionally, apparatus 10 may be operated without inserting a receptacle if it is desire to do a "dry fire." As described in greater detail hereinafter, apparatus 10 cannot be operated unless receptacle 22 is fully inserted into carriage assembly 38. Hence, such a configuration provides a way to prevent coupling of aerosolization mechanism 16 to receptacle 22 unless receptacle 22 is properly inserted.

To aerosolize the medicament, a pump handle 40 is extended away from base unit 12. As described in greater detail hereinafter, when pump handle 40 is extended to a fully extended position and then pushed inwardly back to the home or retracted position (as illustrated in FIGS. 1 and 2), a compressed gas is provided within a cylinder in base unit 12. The compressed gas is then released where it will flow through aerosolization mechanism 16 when a fire button 42 (see FIG. 2) is pressed. When fire button 42 is pressed, carriage assembly 38 is operated to move receptacle 22 into engagement with aerosolization mechanism 16 where holes 44 are pierced into receptacle 22. Just after holes 44 are pierced with aerosolization mechanism 16, the pressurized gas within base unit 12 is released to extract the powdered medicament from receptacle 22, deagglomerate and disperse the powdered medicament, and deliver the powdered medicament in aerosolized form into capture chamber 14 in a manner similar to that described in U.S. Pat. No. 5,740,794, previously incorporated by reference.

As described in greater detail hereinafter, one feature of apparatus 10 is that, in addition to preventing coupling of receptacle 22 to aerosolization mechanism 16 if receptacle 22 is not fully inserted into carriage assembly 38, fire button 42 may not be operated if pump handle 40 has not been extended to the fully extended position. In this way, operation of apparatus 10 is prevented unless the user has fully extended handle 40 so that a proper amount of pressurized gas may be provided (upon retraction of handle 40 to the retracted position) to allow aerosolization mechanism 16 to operate properly.

Hence, apparatus 10 is provided with two compliance features to help ensure the proper production of the aerosolized medicament within capture chamber 14. First, receptacle 22 must be fully inserted into carriage assembly 38. Second, handle 40 must be fully extended to the extended position. If both of these conditions are not satisfied, fire button 42 cannot be pressed to couple receptacle 22 to aerosolization mechanism 16 and to release the pressurized gas to extract the powder from receptacle 22.

When fire button 42 is pressed, carriage assembly 38 is lifted to couple receptacle 22 with aerosolization mechanism 16 which aerosolizes the powder within receptacle 22. Following operation of fire button 42 to aerosolize the medicament, receptacle 22 remains coupled with aerosolization mechanism 16 and therefore cannot removed from carriage assembly 38. To uncouple receptacle 22 from aerosolization mechanism 16, a release button 46 is pressed to lower carriage assembly 38. Receptacle 22 may then be removed from carriage assembly 38 where it will include holes 44.

One particular advantage of releasing the pressurized gas immediately after holes 44 are pierced in receptacle 22 is that the user is prevented from coupling receptacle 22 with aerosolization mechanism 16 and then delaying the release of the pressurized gas. In this way, the powdered medicament within receptacle 22 will not experience prolonged exposure to the environment which may degrade the medicament.

Figure 3:
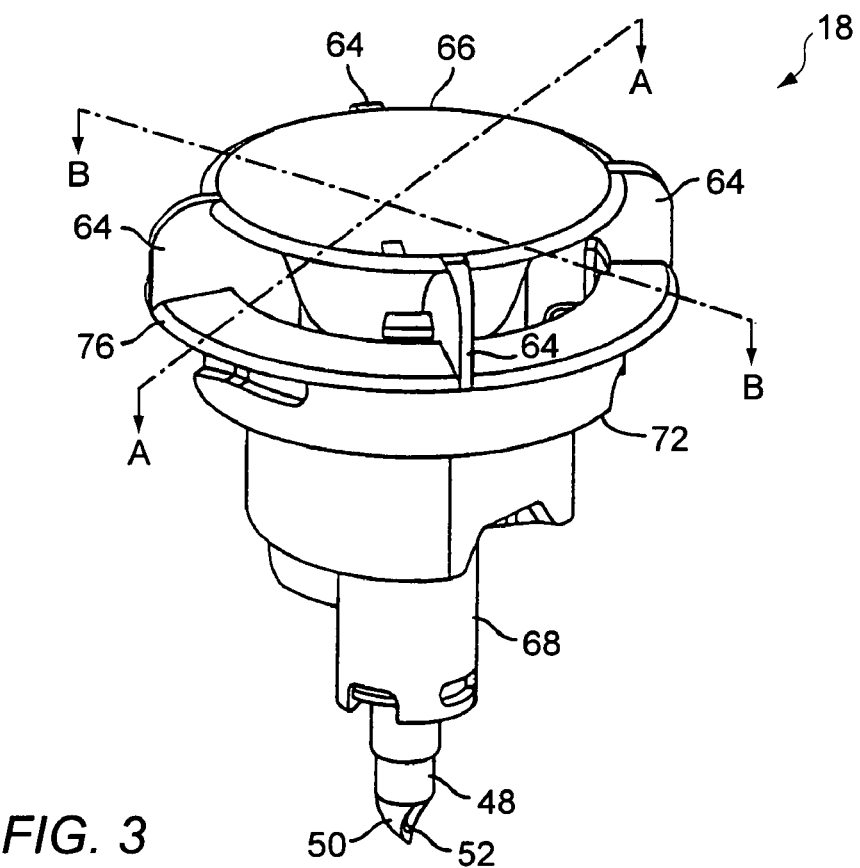
FIG. 3 is a perspective view of an exemplary core of an aerosolization mechanism according to the invention.
Figure 4:
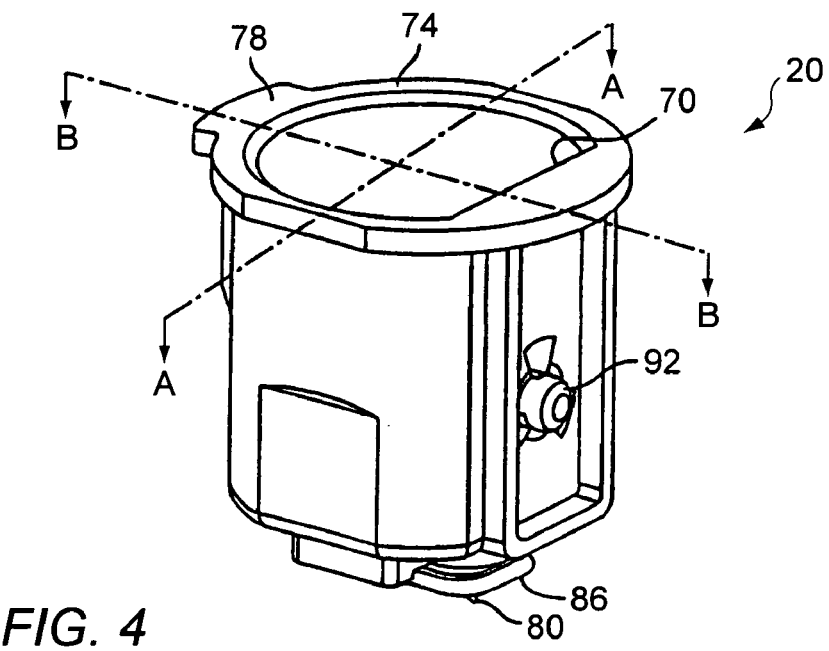
FIG. 4 is a housing of an exemplary aerosolization mechanism which is adapted to receive the core of FIG. 3 according to the invention.
Figure 3A:
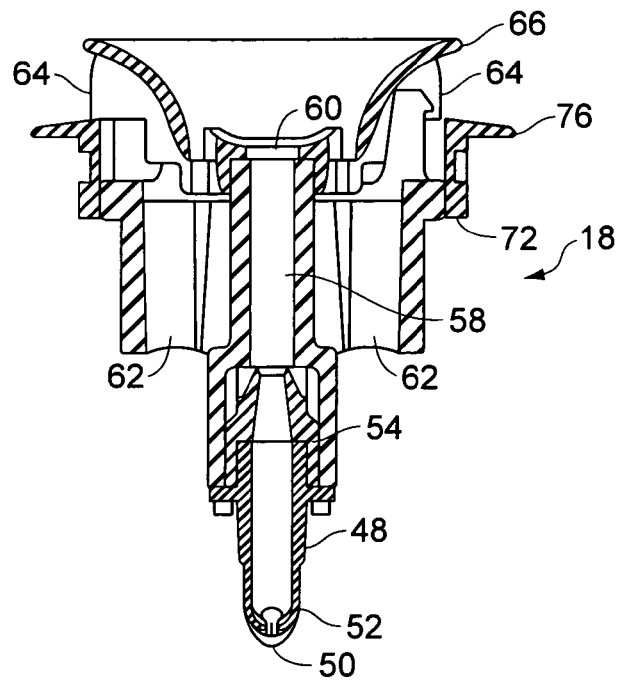
FIGS. 3A and 3B are cross-sectional side views of the core of FIG. 3 taken along lines A-A and B-B, respectively.
Figure 3B:
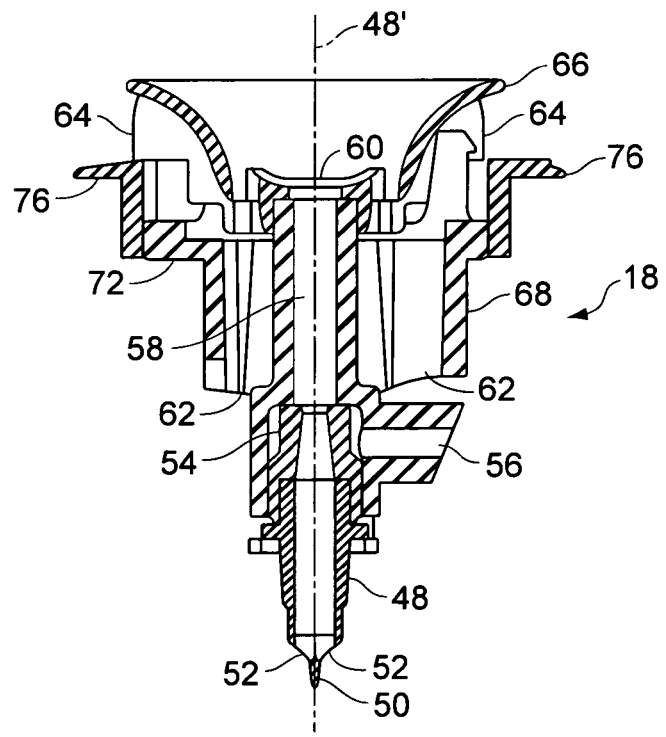
Figure 4A:
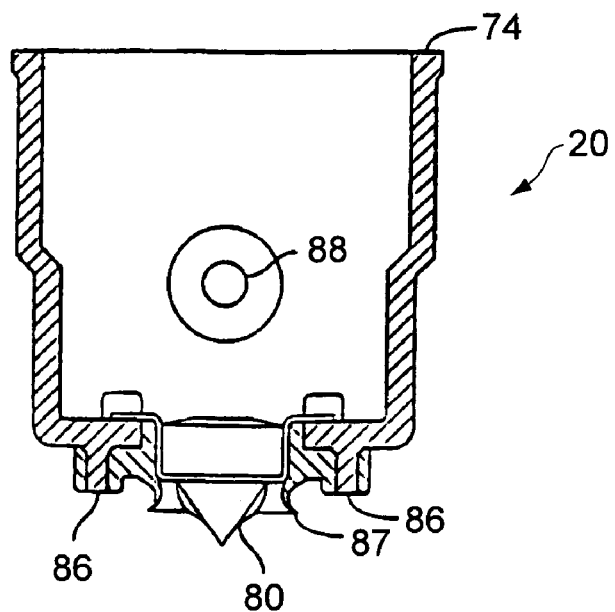
FIGS. 4A and 4B are cross-sectional side views of the housing of FIG. 4 taken along lines A-A and B-B, respectively.
Figure 4B:
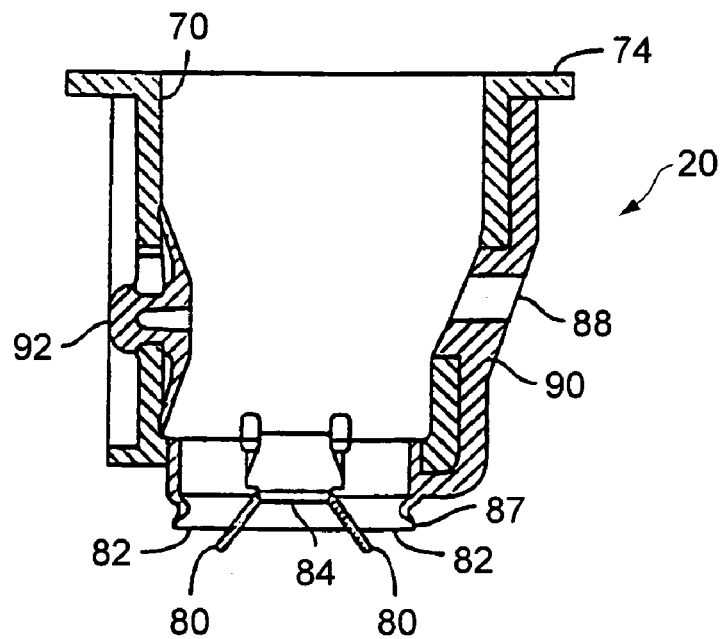
Figure 5:
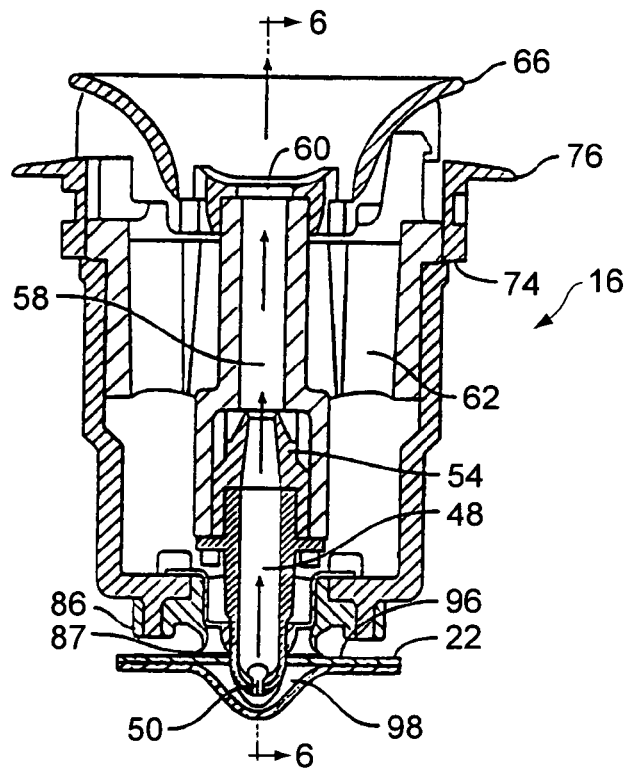
FIG. 5 illustrates the core of FIG. 3A inserted into the housing of FIG. 4A to form an aerosolization mechanism, with the aerosolization mechanism being coupled to a receptacle and showing the manner of powder extraction from the receptacle according to the invention.
Figure 6:
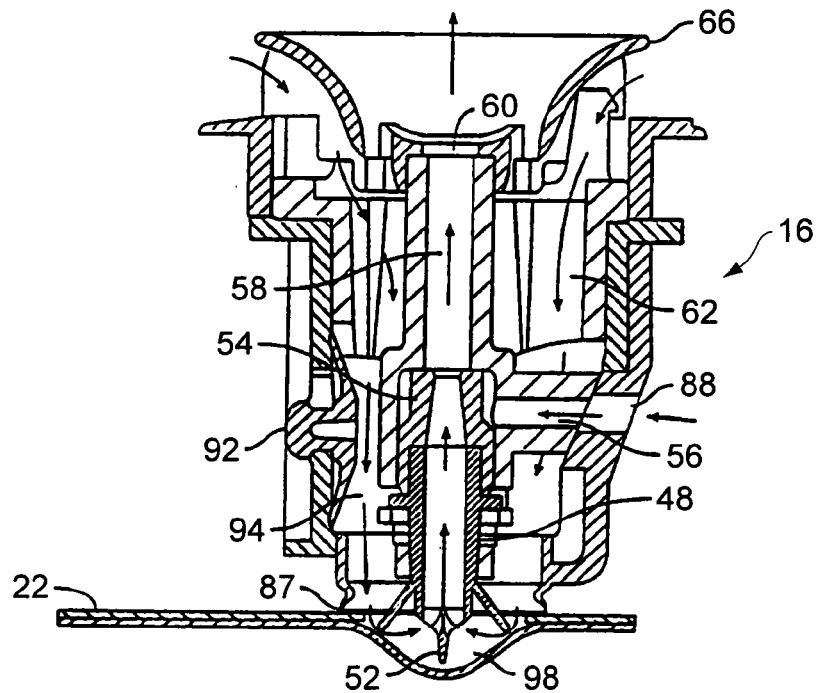
FIG. 6 illustrates the aerosolization mechanism of FIG. 5 taken along lines 6-6.

Referring now to FIGS. 3-3B and 4-4B, construction of aerosolization mechanism 16 will be described in greater detail, with core 18 being illustrated in FIGS. 3-3B and housing 20 being illustrated in FIGS. 4-4B. Core 18 includes an extraction tube 48 having a pointed tip 50 which is adapted to pierce a hole within a receptacle, such as for example the center hole 44 in receptacle 22 (see FIG. 1). Pointed tip 50 includes a pair of apertures 52 which allow the powdered medicament within the receptacle to be drawn into extraction tube 48. Coupled to extraction tube 48 is a nozzle 54 which in turn is in communication with a high-pressure gas inlet 56 (see FIG. 3B). Extending from nozzle 54 is a deagglomeration channel 58 which terminates in an exit opening 60. Core 18 further includes a plurality of air channels 62 which serve both to allow air into a pierced receptacle during aerosolization and to provide an air passageway into the capture chamber when a patient inhales the aerosolized medicament as described in greater detail hereinafter. When coupled with housing 20, core 18 aerosolizes a powdered medicament within a receptacle in a manner similar to that described in U.S. Pat. No. 5,740,794 and Ser. No. 08/309,691, filed Sep. 21, 1994, previously incorporated by reference. Operation of aerosolization mechanism 16 to aerosolize a powdered medicament will also be described in greater detail hereinafter with reference to FIGS. 5-8.

Disposed over air channels 62 by a set of ribs 64 is a curved flange member 66. Curved flange member 66 serves to distribute chase air into the aerosolization chamber with an axial and a radial component to facilitate removal of the aerosolized medicament as described in greater detail hereinafter. Conveniently, ribs 64 divide air channels 62 into four quadrants. As described in greater detail hereinafter, the size of the four quadrants may be varied to vary the volume of air that passes through each of the quadrants.

Core 18 further includes a flat surface 68 which is aligned with a flat surface 70 of housing 20 to facilitate proper alignment of core 18 when inserted into housing 20. When core 18 is inserted into housing 20, an edge 72 of core 18 rests upon a top end 74 of housing 20. Core 18 also includes a lip 76 which rests upon a top end of base unit 12 when aerosolization mechanism 16 is inserted into opening 21 of base unit 12. Conveniently, housing 20 includes a key 78 to assist in proper orientation of aerosolization mechanism 16 into base unit 12.

Referring now to FIGS. 4-4B, construction of housing 20 will be described in greater detail. Housing 20 includes a pair of side punches 80 which are configured to punch a pair of holes into a receptacle, such as the outer holes in receptacle 22 of FIG. 1. Side punches 80 are angled so that they will peel back the receptacle as they enter. A pair of openings 82 are provided in housing 20 and are in fluid communication with air channels 62 when core 18 is inserted into housing 20. In this way, air may travel through air channels 62, through openings 82 and into the receptacle to assist in the extraction of the powdered medicament. Housing 20 further includes a hole 84 (see FIG. 4B) through which pointed tip 50 of core 18 is received when core 18 is coupled to housing 20. A stop 86 is provided on housing 20 and serves to stop penetration of side punches 80 and pointed tip 50 when coupling aerosolization mechanism 16 to a receptacle. A seal 87 is provided to form a seal between aerosolization mechanism 16 and receptacle 22.

As best shown in FIGS. 4A and 4B, a port 88 is disposed in housing 20 and is aligned with high-pressure gas inlet 56 when core 18 is inserted into housing 20. As best shown in FIG. 4B, housing 20 is constructed of a resilient material in the region around port 88 and stop 86 to provide an overmold seal 90. Seal 90 provides a seal between port 88 and a valve through which the high-pressure gas is provided to extract and deagglomerate the powder from the receptacle, and to provide a seal between stop 86 and the receptacle. Overmold seal 90 may be constructed using a two-shot molding process as is known in the art. Further, the angled nature of seal 90 in the vicinity of port 88 assists in properly aligning port 88 with the air flow tube which delivers the pressurized gas through nozzle 54. As best shown in FIGS. 4 and 4B, housing 20 further includes an inlet check valve 92 which allows air into housing 20 when a patient inhales from the capture chamber to extract the aerosolized medicament from the capture chamber. Check valve 92 is constructed as a mushroom valve which opens after experiencing a threshold pressure. Use of such a valve is advantageous in that a pressure drop is created when a patient begins to inhale so that a generally uniform pressure may be produced within a plenum 94 (see FIG. 6). As described in greater detail hereinafter, by providing a generally uniform pressure within plenum 94, the management of air flow into the capture chamber may be better controlled.

One particular advantage of constructing core 18 so that it is removable from housing 20 is that core 18 may be periodically removed and replaced with a new core. In this way, the life of the aerosolization apparatus may be greatly increased. Further, by including the more expensive components on housing 20, the cost of replacing the core can be greatly reduced. Although shown as being constructed from two components, it will be appreciated that aerosolization mechanism 16 may also be constructed as an integral system.

Referring now to FIGS. 5-8, operation of aerosolization mechanism 16 to extract a powdered medicament from receptacle 22, to deagglomerate the powdered medicament, and to deliver the powdered medicament in aerosolized form into a capture chamber will be described. When receptacle 22 is coupled to aerosolization mechanism 16, seal 87 is placed adjacent to a top surface 96 of receptacle 22 to form a seal between aerosolization mechanism 16 and top surface 96. Further, stop 86 engages carriage assembly 38 (see FIG. 10N) to prevent further upward travel of carriage assembly 38. Pointed tip 50 and side punches 80 penetrate top surface 96 and are disposed within a cavity or pocket 98 which holds the powdered medicament. To extract the powdered medicament, a high-pressurized gas is supplied through port 88 and high-pressure gas inlet 56 as shown by the arrows. The high-pressurized gas passes through nozzle 54 causing air to entrain through air channels 62, through pocket 98 and through extraction tube 48 as indicated by the arrows. The entrained air is included in a closed air circuit which includes air in the capture chamber, in the aerosolization mechanism, and in the receptacle. Such a process is essentially identical to that described in U.S. Pat. No. 5,740,794, previously incorporated by reference.

The powdered medicament within extraction tube 48 then enters deagglomeration channel 58 which serves to deagglomerate the powder so that it will be suitable for inhalation. Deagglomeration channel 58 preferably has a constant diameter with a length that is approximately one times the diameter to about ten times the diameter, more preferably three times the diameter to about seven times the diameter, and most preferably at about five times the diameter. As shown in the drawings, deagglomeration channel 58 terminates abruptly at exit opening 60. In this way, a "dump diffuser" is provided so that the gas flow out of deagglomeration channel 58 will tend to further break apart the powdered medicament and not slow down. In this manner, the dispersement of the aerosolized medicament into the capture chamber is improved.

Figure 7:
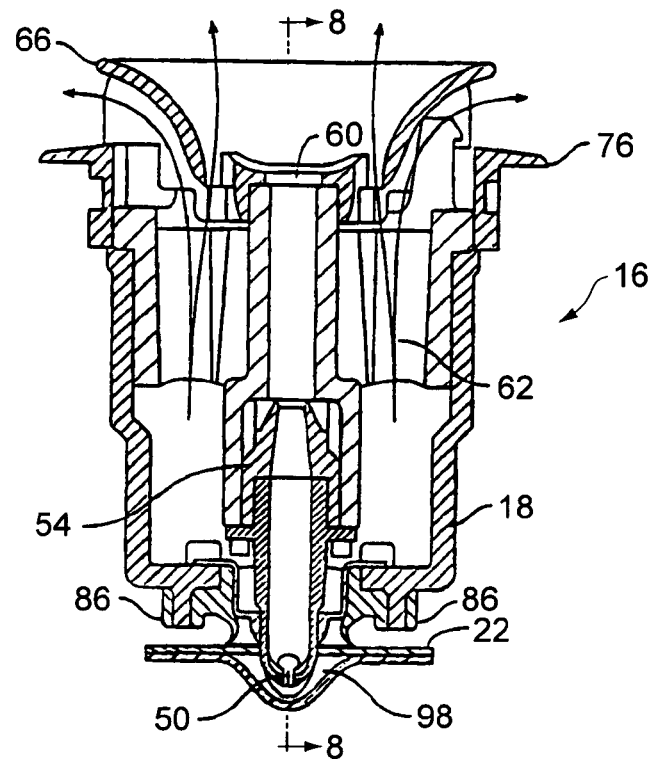
FIG. 7 illustrates the aerosolization mechanism of FIG. 5 showing the manner of air distribution as a patient inhales to draw air through the aerosolization mechanism according to the invention.
Figure 8:
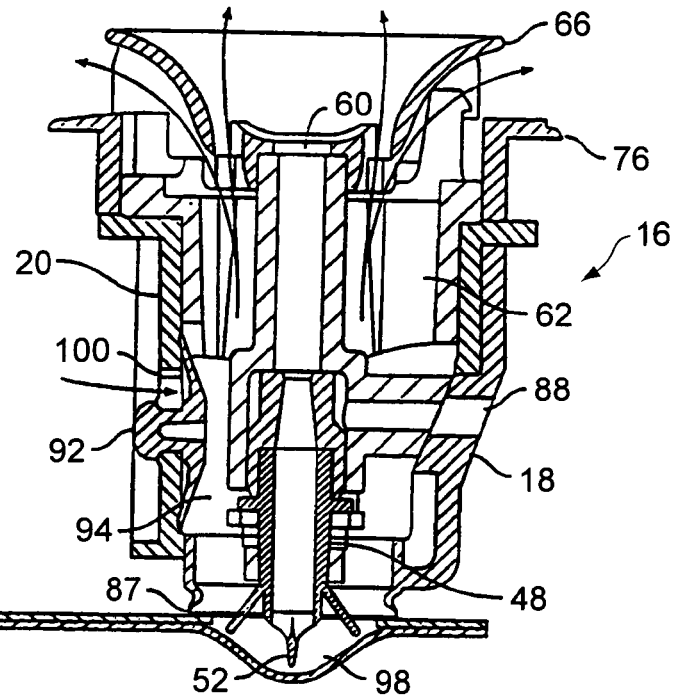
FIG. 8 illustrates the aerosolization mechanism of FIG. 7 taken along lines 8-8.

Following dispersement of the powdered medicament into the capture chamber, the patient inhales to extract the powdered medicament from the capture chamber, causing chase air to flow through aerosolization mechanism 16 as illustrated in FIGS. 7 and 8. When the patient inhales, replacement (or chase) air needs to be introduced into the capture chamber to allow the aerosolized medicament to be removed. Such chase air passes through aerosolization mechanism 16 after entering into plenum 94 through inlet check valve 92. An opening 100 (see FIG. 8) is provided in housing 20 to allow the chase air to open inlet valve 92 and pass through air channels 62 as indicated by the arrows.

Aerosolization mechanism 16 is designed so that the chase air entering the capture chamber is managed to minimize the amount of mixing of the aerosolized medicament with the entering chase air. In this way, the powdered medicament may be extracted from the chamber in a bolus followed by the chase air passing through aerosolization mechanism 16. Such distribution of the chase air in the capture chamber is accomplished in part by providing check valve 92 which provides a pressure drop so that the air within plenum 94 will be at a substantially constant pressure. Proper air distribution is also provided by curved flange member 66 which divides the air flow within air channels 62 into an axial and a radial component. Hence, as the patient inhales from the mouthpiece of the capture chamber, the chase air flowing through aerosolization mechanism 16 is distributed into the capture chamber in a manner such that the amount of air that mixes with the powdered medicament is minimized.

Figure 9:
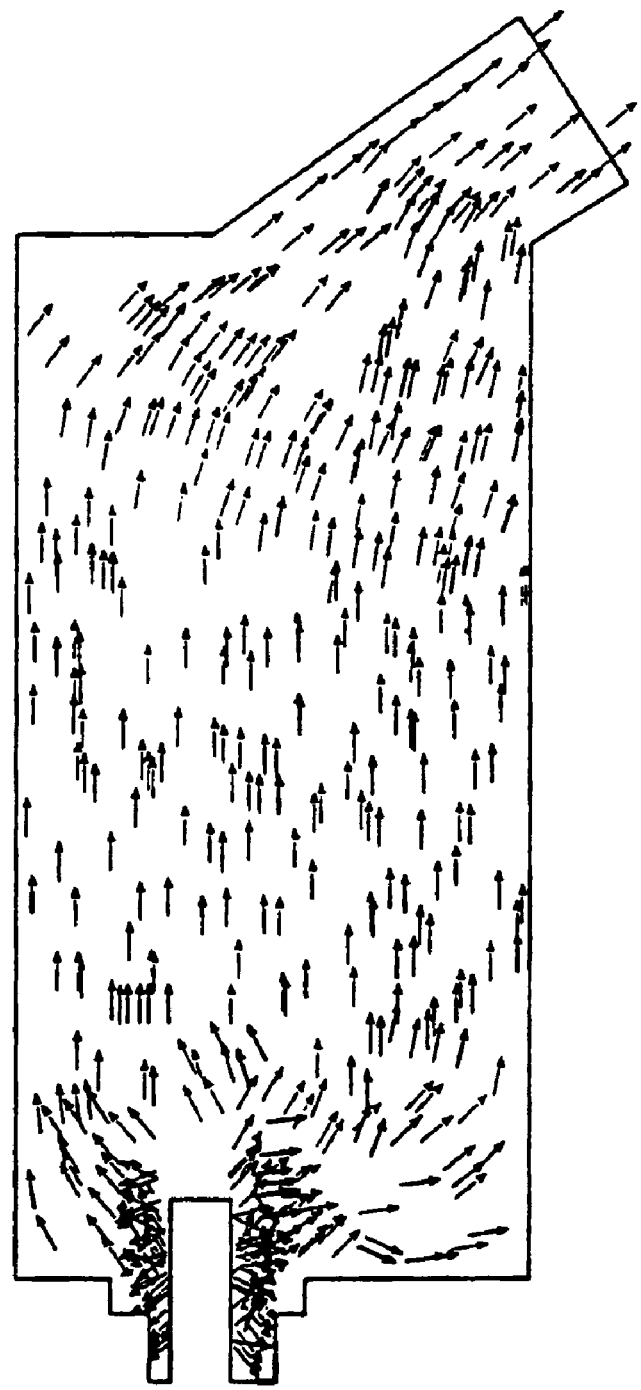
FIG. 9 is a schematic diagram of an air capture chamber showing the pattern of air flow that is produced upon inhalation by a patient according to the invention.
Figure 9A:
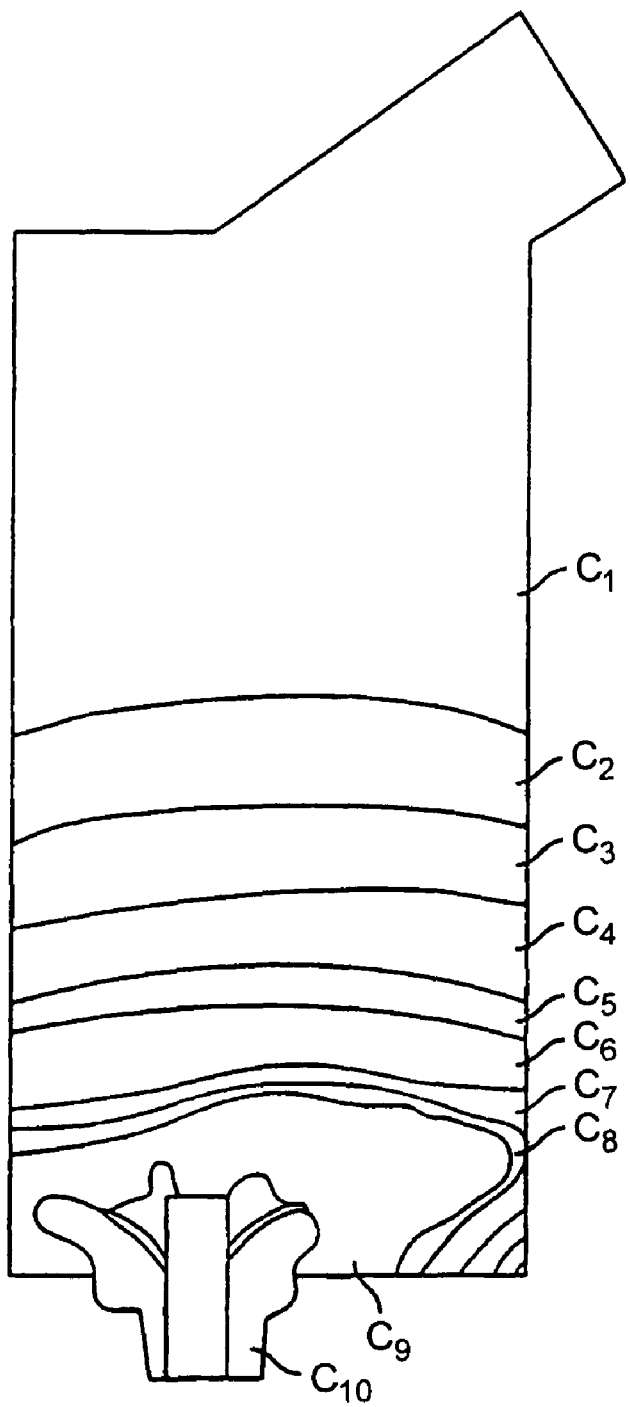
FIG. 9A is a schematic diagram of a capture chamber illustrating removal of an aerosolized medicament upon inhalation by a patient according to the invention.

Such a feature is illustrated in FIGS. 9 and 9A which illustrate how the powdered medicament remains in a bolus that is evenly removed from the capture chamber. In FIG. 9, the arrows illustrate the flow path of the incoming chase air as it moves through the capture chamber. As shown, the flow paths are generally parallel, indicating that substantially none of the chase air mixes with the aerosolized medicament. FIG. 9A illustrates the mass fraction of air within a capture chamber at approximately 100 milliseconds after inhalation is initiated. Contours C1-C10 illustrate contours of mass fraction of air. Contour C1 illustrates the powdered medicament bolus, and contour C10 illustrates the incoming chase air. As shown, almost no mixing of the incoming chase air occurs with the bolus. As a result, the bolus is lifted evenly upward and out of the mouthpiece where it will be followed by the chase air. In this manner, in the first part of the tidal volume, the patient receives the powdered medicament. During the remainder of the tidal volume, the chase air flows into the patient's lungs to assist in delivering the powdered medicament into the deep regions of the lungs. Hence, the front end of the inhalation cycle is employed to extract the powdered medicament from the chamber while the remainder of the inhalation cycle serves to further deliver the powdered medicament to the lungs.

As illustrated in FIG. 1, aerosolization mechanism 16 is offset from a center of base unit 12. To produce the proper air flow into the aerosolization chamber, the location of ribs 64 (see FIG. 3) may be varied to allow more chase air to pass through the quadrant facing the larger area of the capture chamber so that the air flow may be more evenly distributed within the capture chamber.

Figure 10:
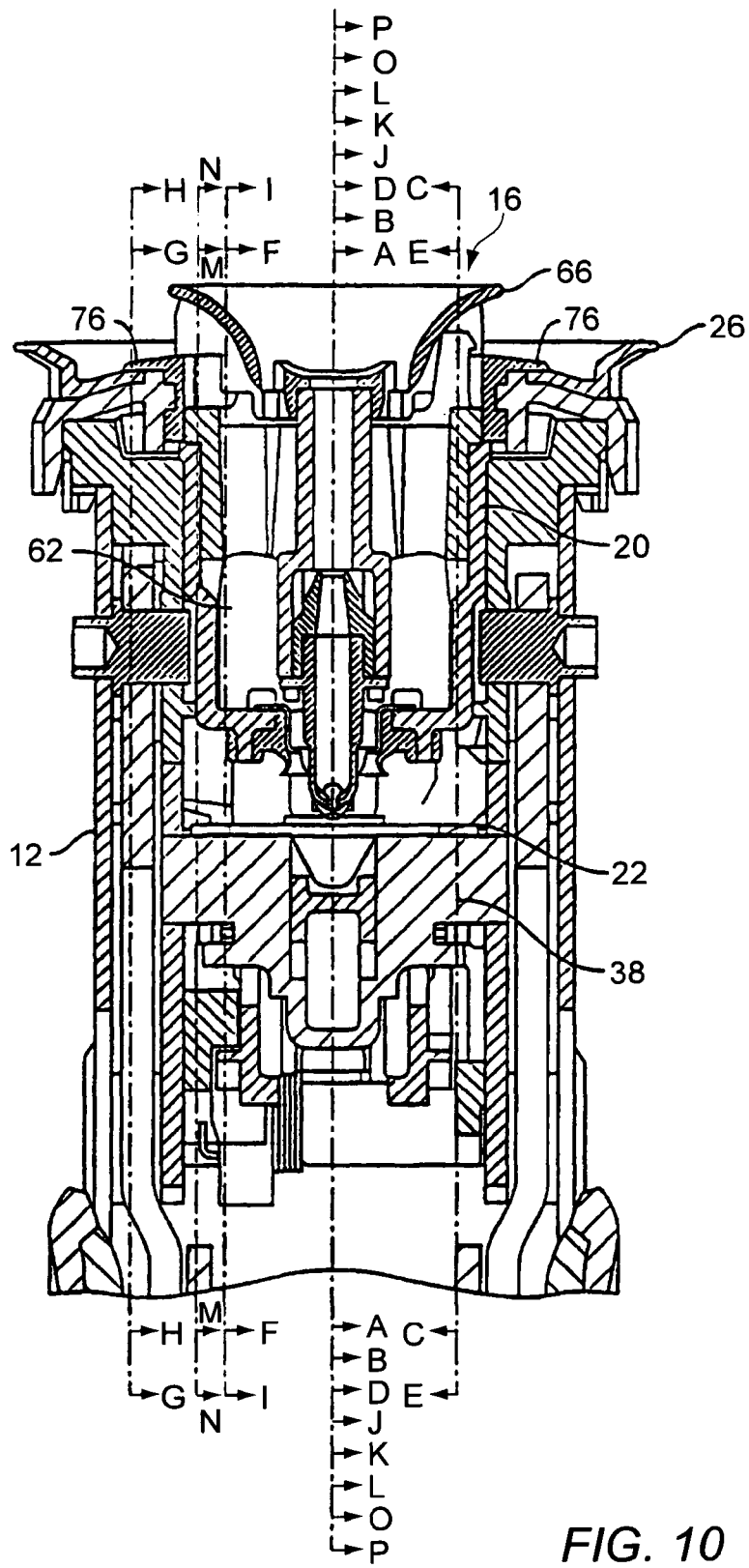
FIG. 10 is a cross-sectional side view of a base unit of the apparatus of FIG. 1 taken along lines 10-10 (when the aerosolization mechanism and a receptacle are inserted into the base unit).

Referring now to FIG. 10, a cross-sectional side view of apparatus 10 of FIG. 1 taken along lines 10-10 is shown. In the view of FIG. 10, aerosolization mechanism 16 is disposed within base unit 12, and receptacle 22 is inserted into carriage assembly 38. FIG. 10 is provided to serve as a reference to illustrate the various views of FIGS. 10A-10P, which describe the method of operation of apparatus 10. As previously mentioned, apparatus 10 includes a receptacle interlock that prevents operation of fire button 42 if receptacle 22 is only partially inserted into carriage assembly 38. Such a feature is illustrated in FIGS. 10A-10E. For convenience of illustration, aerosolization mechanism 16 is not shown in base unit 12.

Figure 10A:
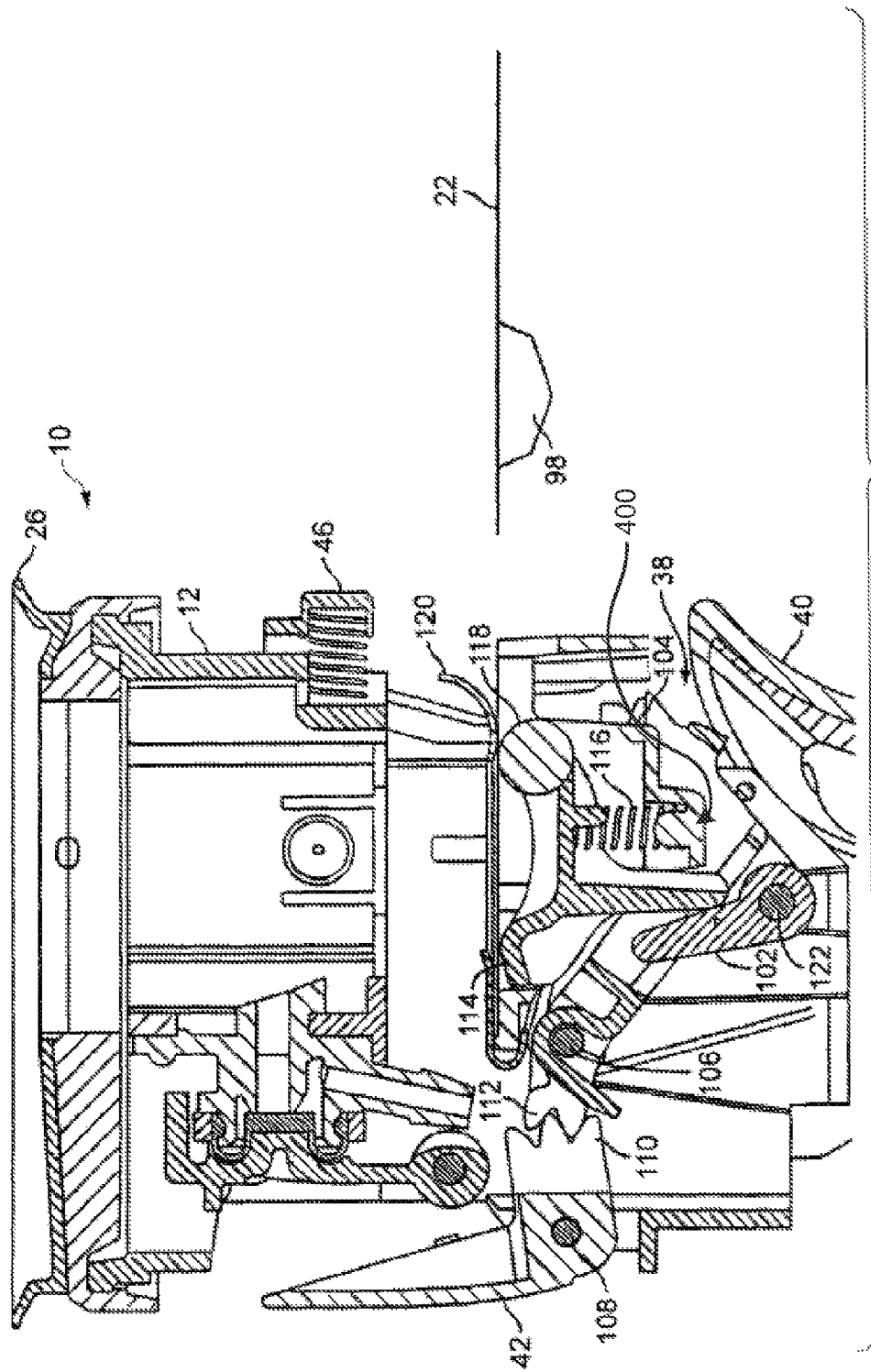
FIGS. 10A-10P illustrate cross-sectional side views of the base of FIG. 10 taken along lines A-A through P-P, respectively (with the base unit being in various states of operation).

In FIG. 10A, base unit 12 is in a home or ready state. In the ready state, a receptacle interlock 102 is in a rest position. When in the rest position, a lifter 104 of carriage assembly 38 is able to pivot upwardly about a pivot pin 106. Fire button 42 is also pivotally attached to base unit 12 by a pivot pin 108 which allows a set of gear teeth 110 on fire button 42 to move when fire button 42 is depressed. In turn, a set of gear teeth 112 on lifter 104 are moved by gear teeth 110 to lift lifter 104 vertically upward. Base unit 12 further includes a sensor arm 114 which is biased by a spring 116 in a rest position. As described in greater detail hereinafter, when sensor arm 114 is in the rest position, receptacle interlock 102 is also in the rest position where fire button 42 may be operated to lift lifter 104. Conveniently, sensor arm 114 includes a roller 118 over which receptacle 22 passes when inserted into carriage assembly 38. Although shown with a roller, it will be appreciated that a stationary mechanism may also be disposed in place of roller 118. Conveniently, a guide 120 is provided to facilitate introduction of receptacle 22 into carriage assembly 38.

Figure 10B:
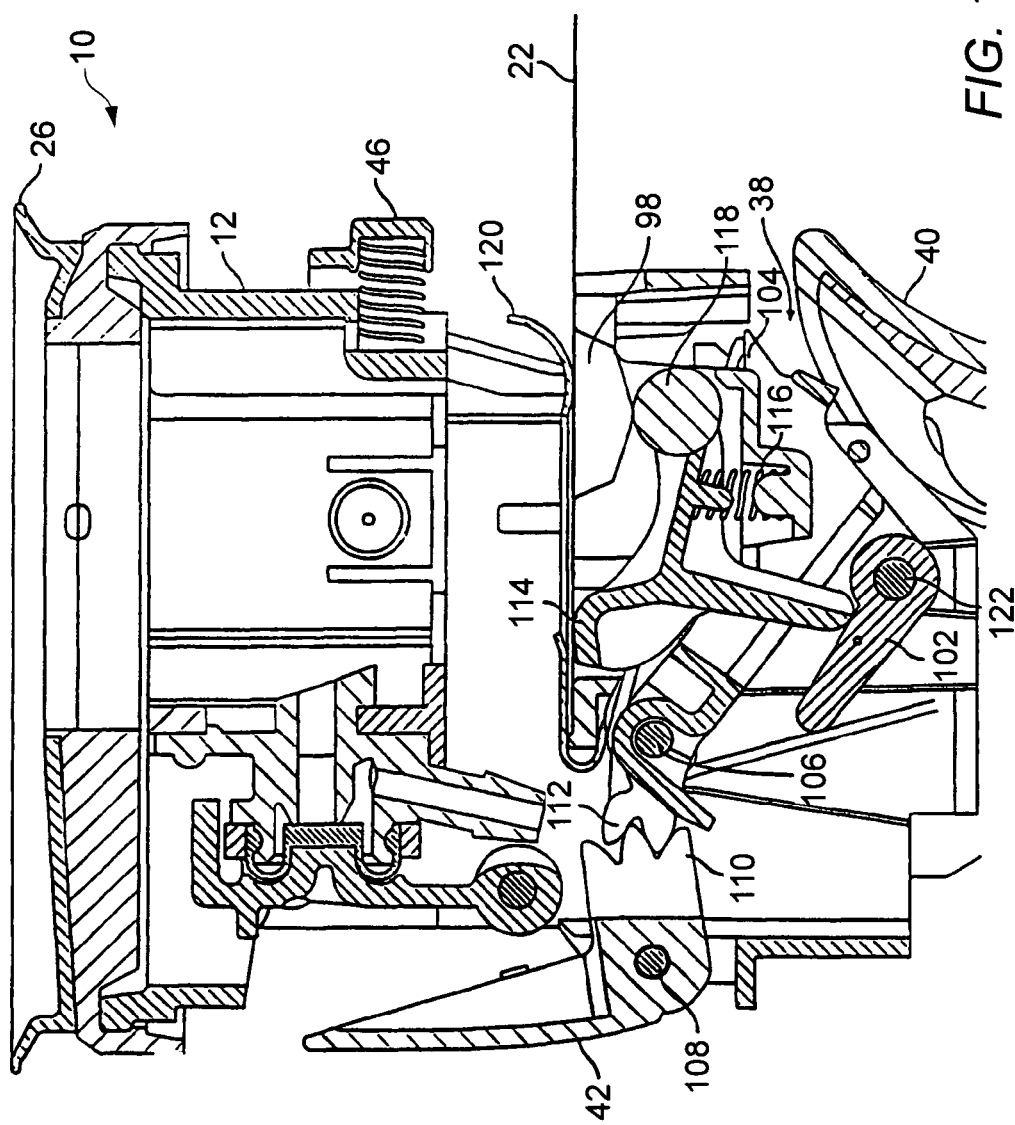
Figure 10C:
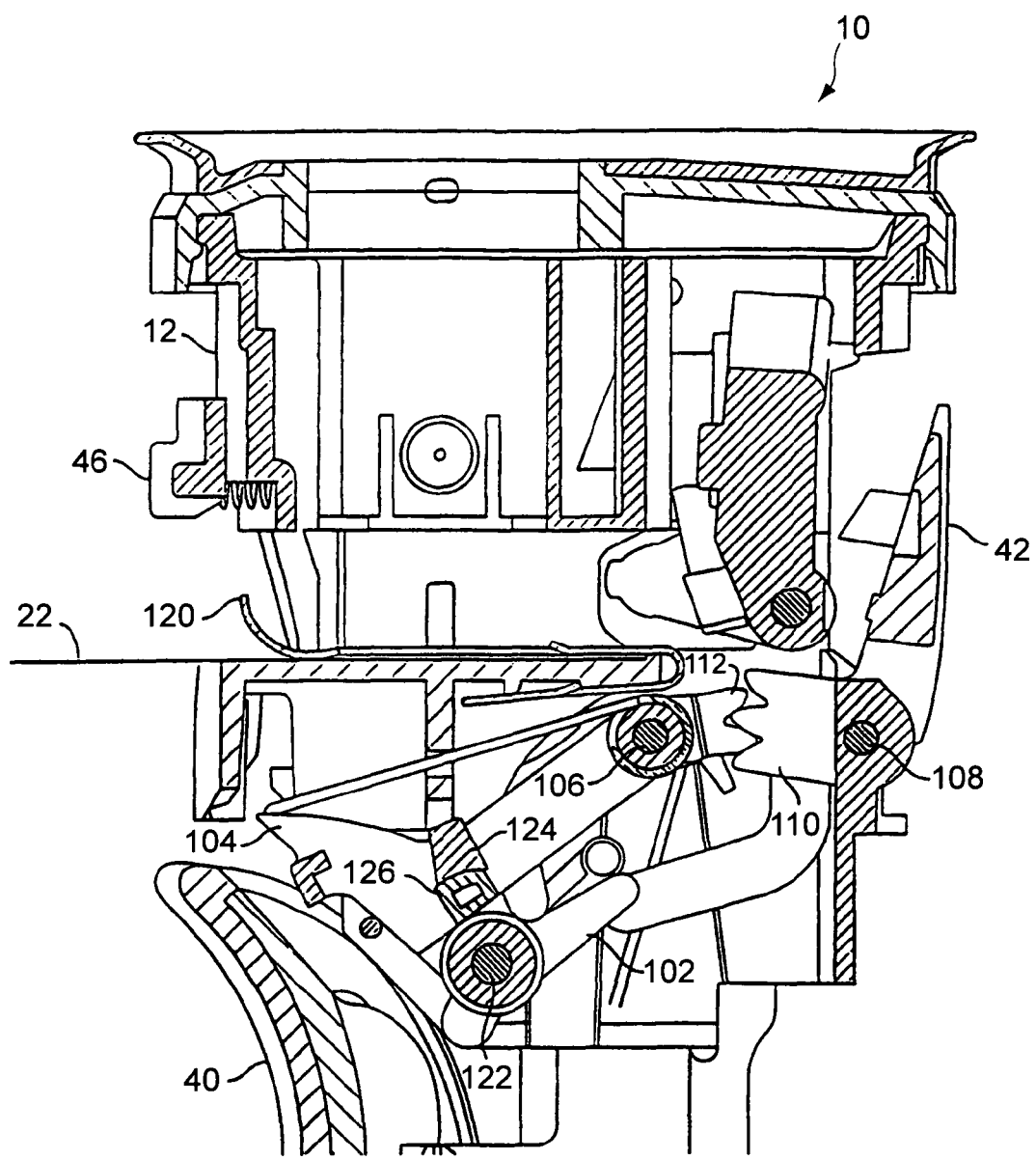

As shown in FIG. 10B, receptacle 22 is partially inserted into carriage assembly 38. When only partially inserted, pocket 98 of receptacle 22 contacts roller 118, causing spring 116 to compress and sensor arm 114 to pivot downward as shown. In turn, sensor arm 114 pivots receptacle interlock 102 about a pivot pin 122. As shown in FIG. 10C, receptacle interlock 102 includes a latch 124 which moves over a boss 126 on lifter 104. When latch 124 is disposed over boss 126, lifter 104 is unable to pivot about pivot pin 106. In turn, fire button 42 is unable to be depressed. Hence, if receptacle 22 is only partially inserted as illustrated in FIG. 10B, fire button 42 may not be operated to lift carriage assembly 38, thereby preventing receptacle 22 from being coupled with aerosolization mechanism 16.

Figure 10D:
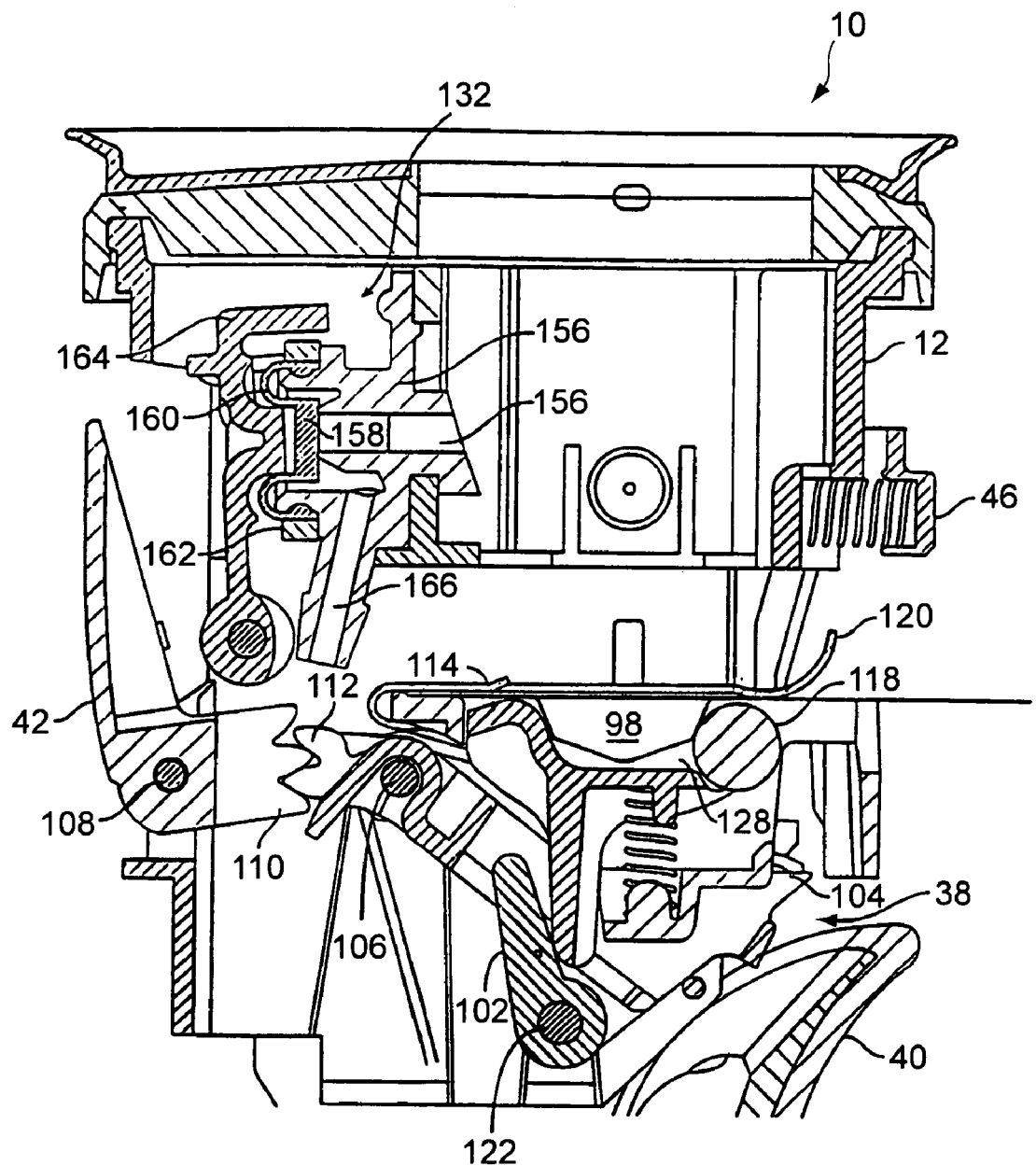
Figure 10E:
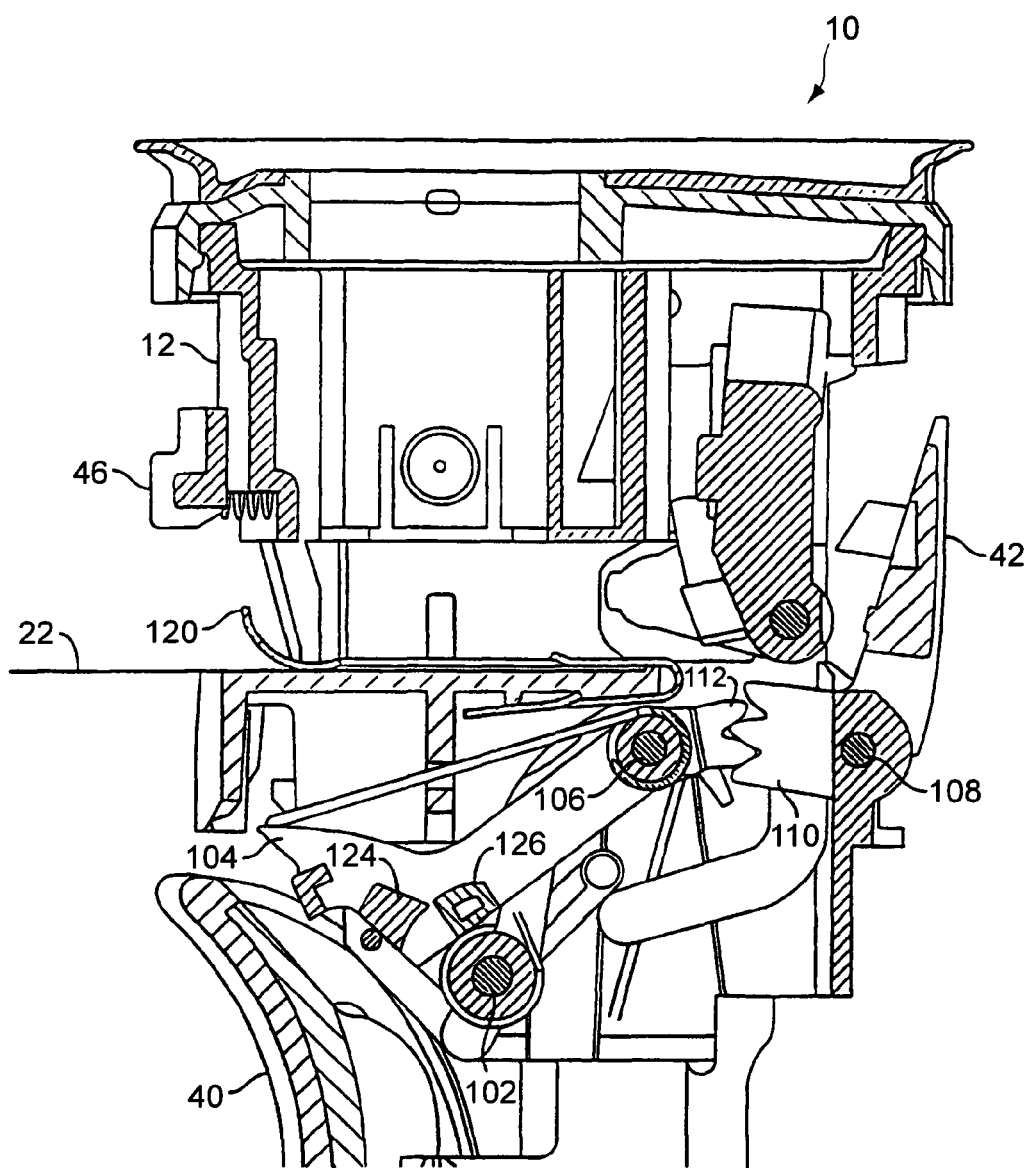
Figure 10F:
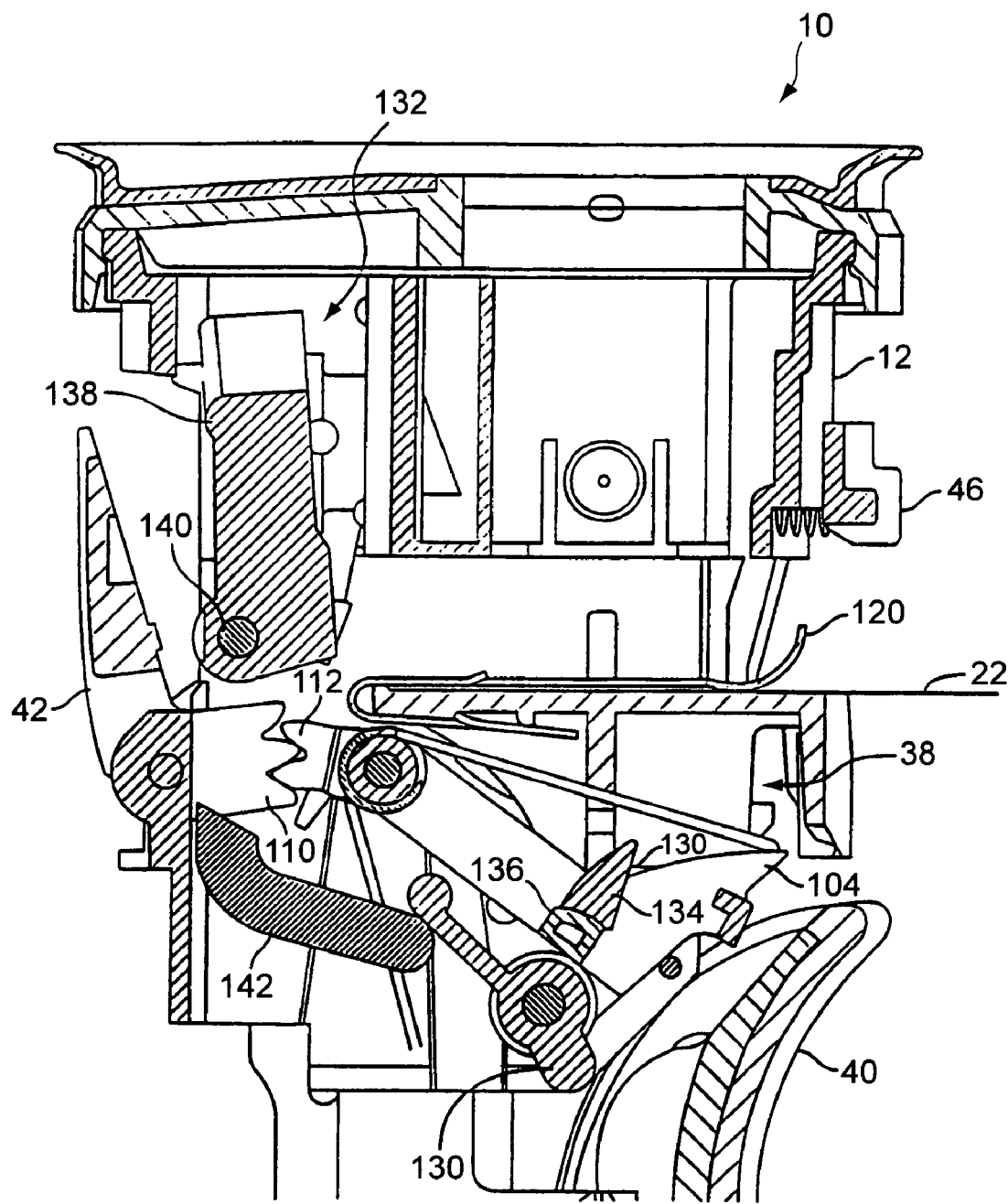
Figure 10G:
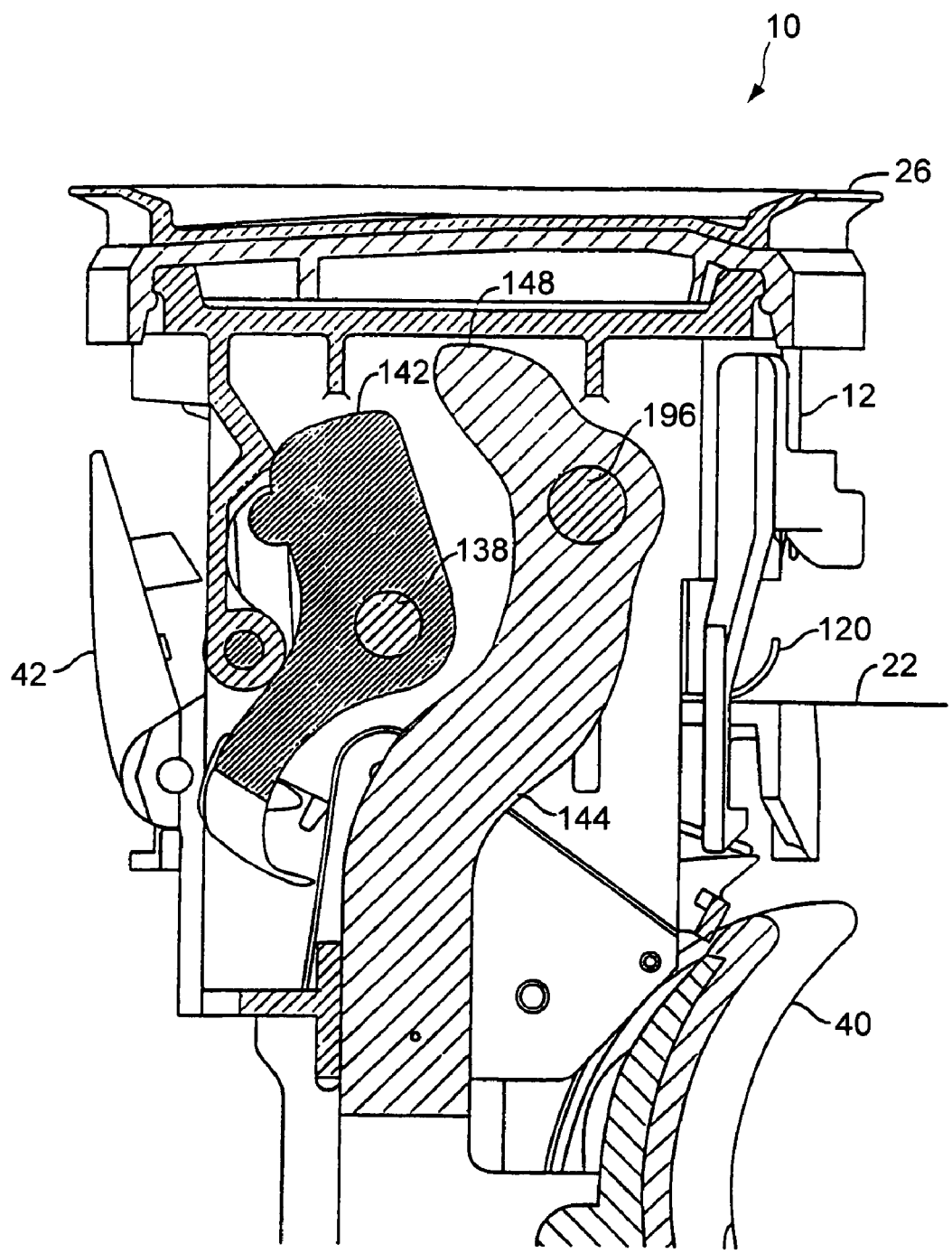

When receptacle 22 is fully inserted into carriage assembly 38, pocket 98 is positioned beyond roller 118 and is disposed within a well 128 of sensor arm 114. When pocket 98 is disposed within well 128, spring 116 moves sensor arm 114 back to the rest position as illustrated in FIG. 10D. In turn, receptacle interlock 102 pivots back to the rest position. As illustrated in FIG. 10E, when receptacle interlock 102 is rotated back to the rest position, latch 124 is now clear of boss 126 on lifter 104. In this way, lifter 104 is not restricted by receptacle interlock 102. However, as described in greater detail hereinafter, fire button 42 may still not be operated until a valve interlock is released.

In summary, sensor arm 114 and receptacle interlock 102 serve to prevent operation of fire button 42 if receptacle 22 is only partially inserted. If not inserted, or if fully inserted, receptacle interlock 102 is in a rest position where it does not prevent movement of lifter 104 of carriage assembly 38. When a valve interlock, as described hereinafter, is released, fire button 42 may be depressed to move carriage assembly 38 upward so that receptacle 22 may engage with aerosolization mechanism 16. In this way, a compliance feature is provided to prevent operation of aerosolization apparatus 10 if receptacle 22 is not correctly inserted. Moreover, by providing well 128 in sensor arm 114, an alignment mechanism is provided to ensure that pocket 98 will be properly aligned with aerosolization mechanism 16. In this way, receptacle 22 is properly coupled to aerosolization mechanism 16 each time apparatus 10 is operated to produce the aerosolized medicament.

Referring now to FIGS. 10F-10K, operation of a valve interlock 130 will be described. In order to extract an aerosolization medicament within receptacle 22, a pressurized gas must be supplied to aerosolization mechanism 16 (see FIG. 10). As described in greater detail hereinafter, the pressurized gas is provided by operating handle 40 to pressurize the gas within a cylinder. Before the gas can be pressurized in the cylinder, a valve 132 must be closed and locked to allow the pressure to build up within the cylinder. As shown in FIG. 10F, valve interlock 130 is in a ready state. In the ready state, valve 132 is unlocked and valve interlock 130 prevents operation of fire button 42. As described in greater detail hereinafter, valve interlock 130 is not released to allow fire button 42 to be operated until handle 40 is extended to a fully extended position. Upon reaching the fully extended position, valve 132 is locked and valve interlock 130 is released so that, as handle 40 is moved back to the home or retracted position, the precise amount of pressurized gas is produced and may be released upon operation of fire button 42.

As shown in FIG. 10G, receptacle 22 is fully inserted so that receptacle interlock 102 (see FIG. 10A) is in the ready state and is not engaged with lifter 104. Handle 40 is in the home or retracted position and valve 132 is unlocked so that there is no pressurized gas within base unit 12. As shown in FIG. 10F, valve interlock 130 includes a latch 134 which is positioned over a boss 136 on lifter 104 when valve interlock 130 is in the rest or ready state. In the rest state, an actuator arm 138, which is pivotally attached to base unit 12 by a pivot pin 140, is in an unlocked position so that valve 132 is unlocked. Base unit 12 further includes a valve set arm 142. As shown in FIGS. 10F and 10G, valve set arm 142 is in an open position where valve set arm 142 engages valve interlock 130 to position latch 134 over boss 136. As best shown in FIG. 10G, handle 40 includes a pump link 144 which is pivotally attached to base unit 12 by a pivot pin 146. Pump link 144 includes a nose 148 which is spaced apart from valve set arm 142 when in the open position.

As handle 40 is extended from the home position toward an extended position, pump link 144 pivots about pivot pin 146 causing nose 148 to engage valve set arm 142, as illustrated in FIG. 10H. Base unit 12 includes a chassis 150 having a boss 152. As nose 148 pushes on valve set arm 142, valve set arm 142 slides under boss 152 on chassis 150 to lock valve set arm 142 in place. In turn, actuator arm 138 is rotated about pivot pin 140 (see FIG. 10I) to move actuator arm 138 to a locked position. In this way, valve 132 (see FIG. 10I) is closed and locked so that, as handle 40 is moved back toward base unit 12, a pressurized gas may be produced.

As best illustrated in FIG. 10I, as handle 40 is moved to the fully extended position, actuator arm 138 is moved over center to the locked position where valve 132 is closed and locked. In the fully extended position, valve set arm 142 rotates valve interlock 130 to clear latch 134 from boss 136. At this point, both valve interlock 130 and receptacle interlock 102 are disengaged so that fire button 42 may be operated to operate carriage assembly 38 and to open valve 132 to allow the pressurized gas to be delivered to aerosolization mechanism 16 as described in greater detail hereinafter.

Referring now to FIG. 10J, construction of valve 132 will be described in greater detail. In FIG. 10J, receptacle is fully inserted and handle 40 has moved to the fully extended position so that both interlocks 130 and 102 have been released. Valve 132 is constructed of a housing 154 having a passage 156 which is aligned with port 88 (see FIG. 6) when aerosolization mechanism is inserted into base unit 12. Disposed across passage 156 is a valve seat 158. Extending from valve seat 158 is a rolling diaphragm 160 which terminates in an O-ring 162. In FIG. 10J, a valve actuator 164 of actuator arm 138 (see FIG. 10I) is firmly pressed against valve seat 158. As such, valve 132 is in the closed, locked position. Housing 154 further includes a lumen 166 for receiving a high pressurized gas from a pressurization cylinder within base unit 12 as described in greater detail hereinafter. Conveniently, a fitting 168 is provided on housing 154 to allow a tube to be coupled to housing 154.

When valve 132 is in the closed and locked position, gasses are prevented from travelling from lumen 166 through passage 156. As such, when handle 40 is moved back to the home or retracted position, a pressurized gas will be produced. When valve 132 is opened, the high pressurized gas will pass through passage 156 and into aerosolization mechanism 16 to extract the powdered medicament from receptacle 22.

Referring back to FIG. 10D, valve actuator 164 is shown in an unlocked position where handle 40 has not yet been fully extended. In the unlocked position, valve seat 158 still covers passage 156. In this way, when handle 40 is being extended, air is prevented from being drawn through passage 156 and lumen 166. Instead, the pressurization cylinder which pressurizes the air upon operation of handle 40 is filled with air through a check valve in a bottom of base unit 12 as described in greater detail hereinafter. In this manner, any residual powdered medicament which is disposed within aerosolization mechanism 16 will be generally prevented from being drawn through valve 132 and into the pressurization cylinder where it may hinder operation of apparatus 10. Although in the closed state prior to full extension of handle 40, valve seat 158 does not provide a seal to allow pressurized gas to be produced within the cylinder until valve actuator 164 is in the locked position. In this manner, if handle 40 is only partially extended and then moved back to the home position, gasses from the cylinder will be free to move through lumen 166 and through valve 132.

Referring now to FIG. 10K, apparatus 10 is shown with aerosolization mechanism 16 inserted into base, unit 12. Receptacle 22 is fully inserted and handle 40 has been moved back to the home position after being fully extended so that both interlocks 102 and 130 have been released. With both interlocks clear, fire button 42 is ready to be pushed to begin the aerosolization process. As shown, when receptacle 22 is fully inserted, pocket 98 is aligned with pointed tip 50 and side punches 80.

Figure 10H:
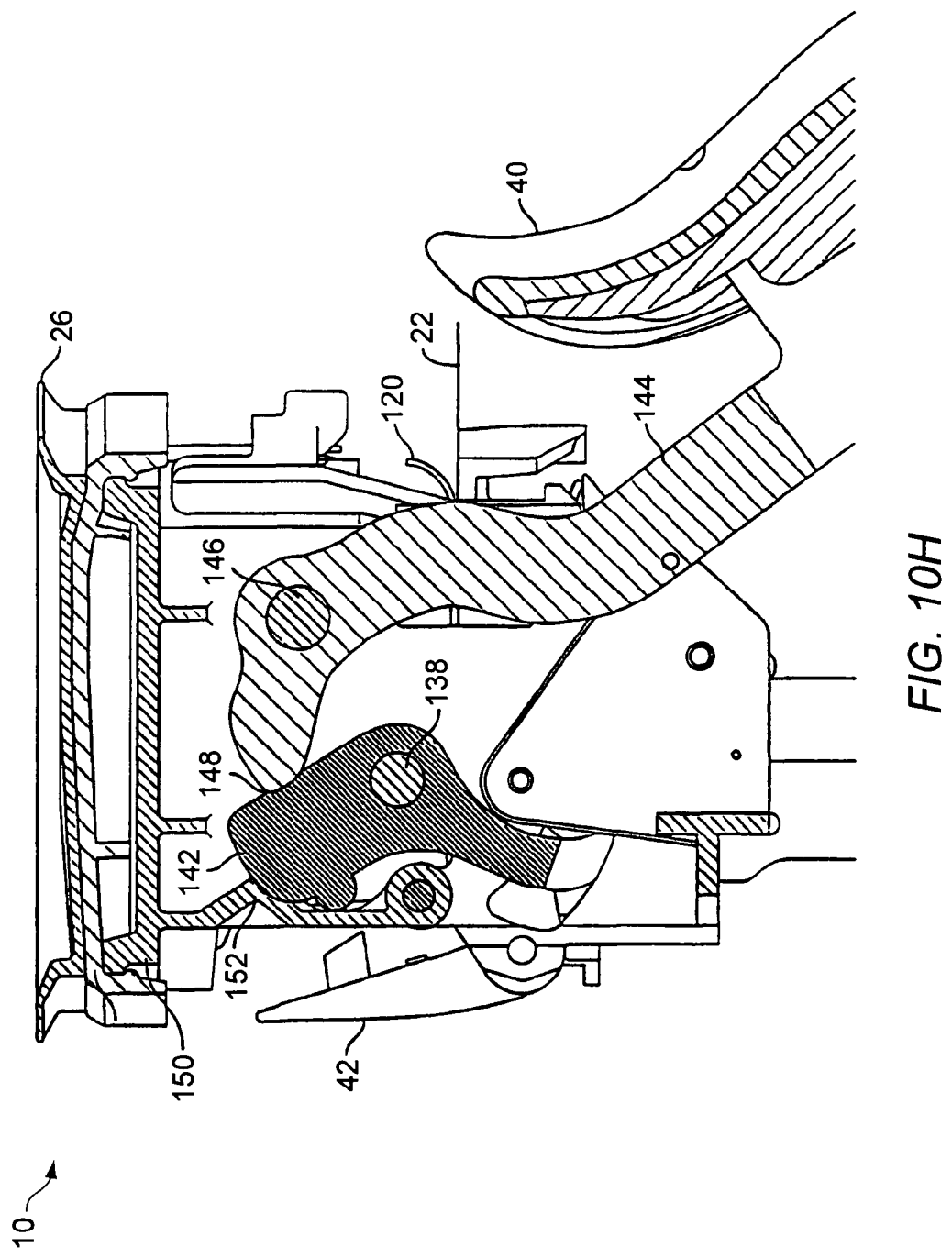
Figure 10I:
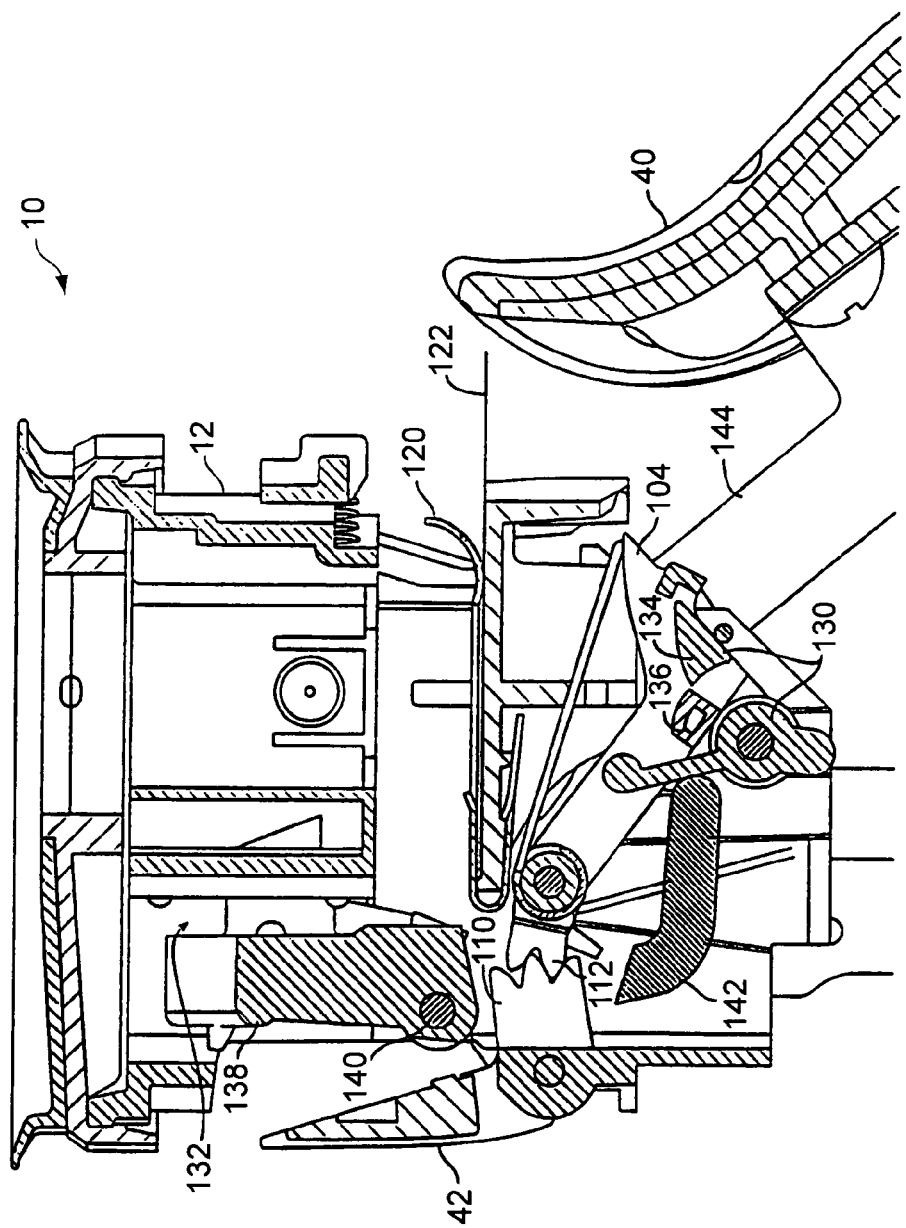
Figure 10J:
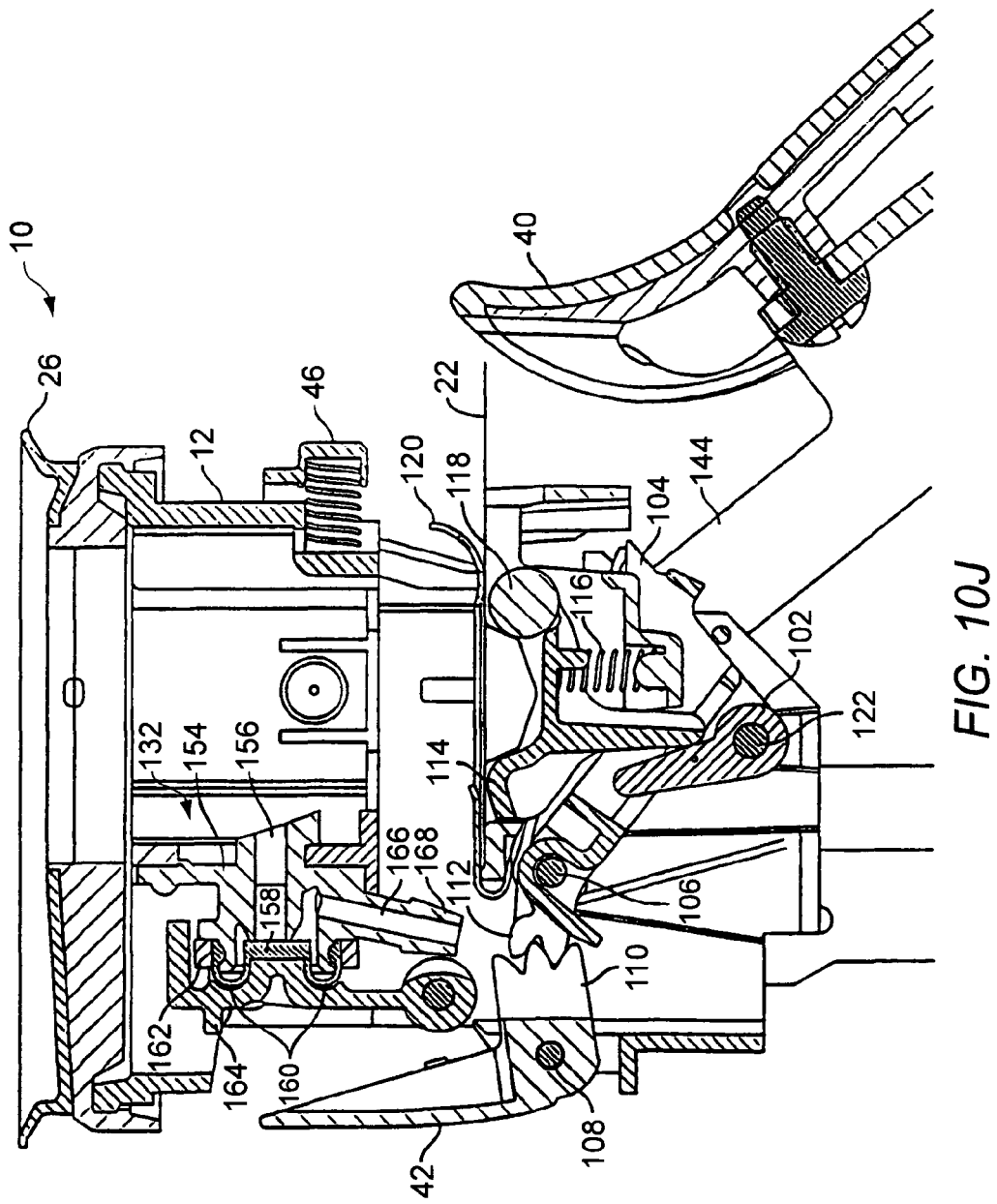
Figure 10K:
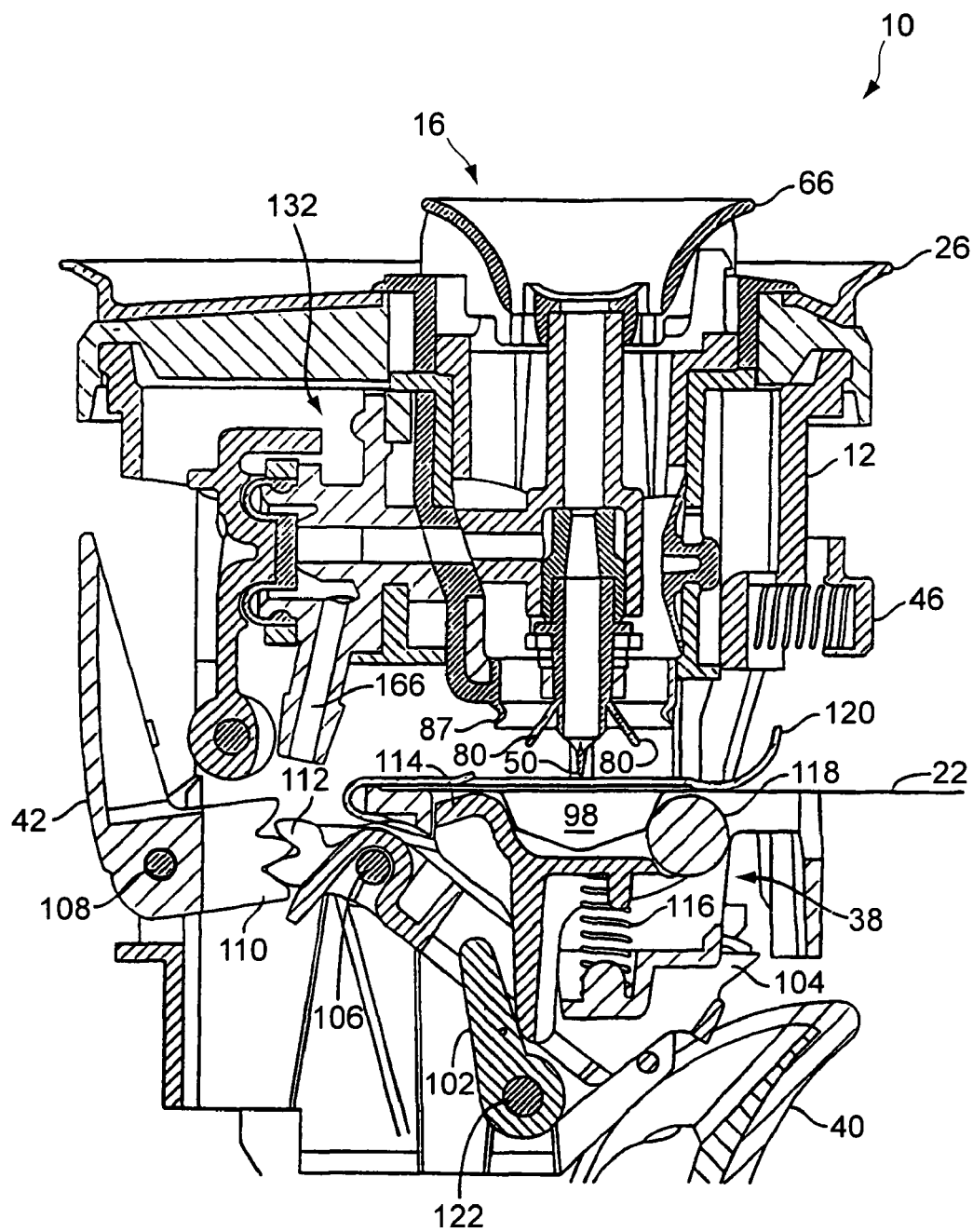
Figure 10L:
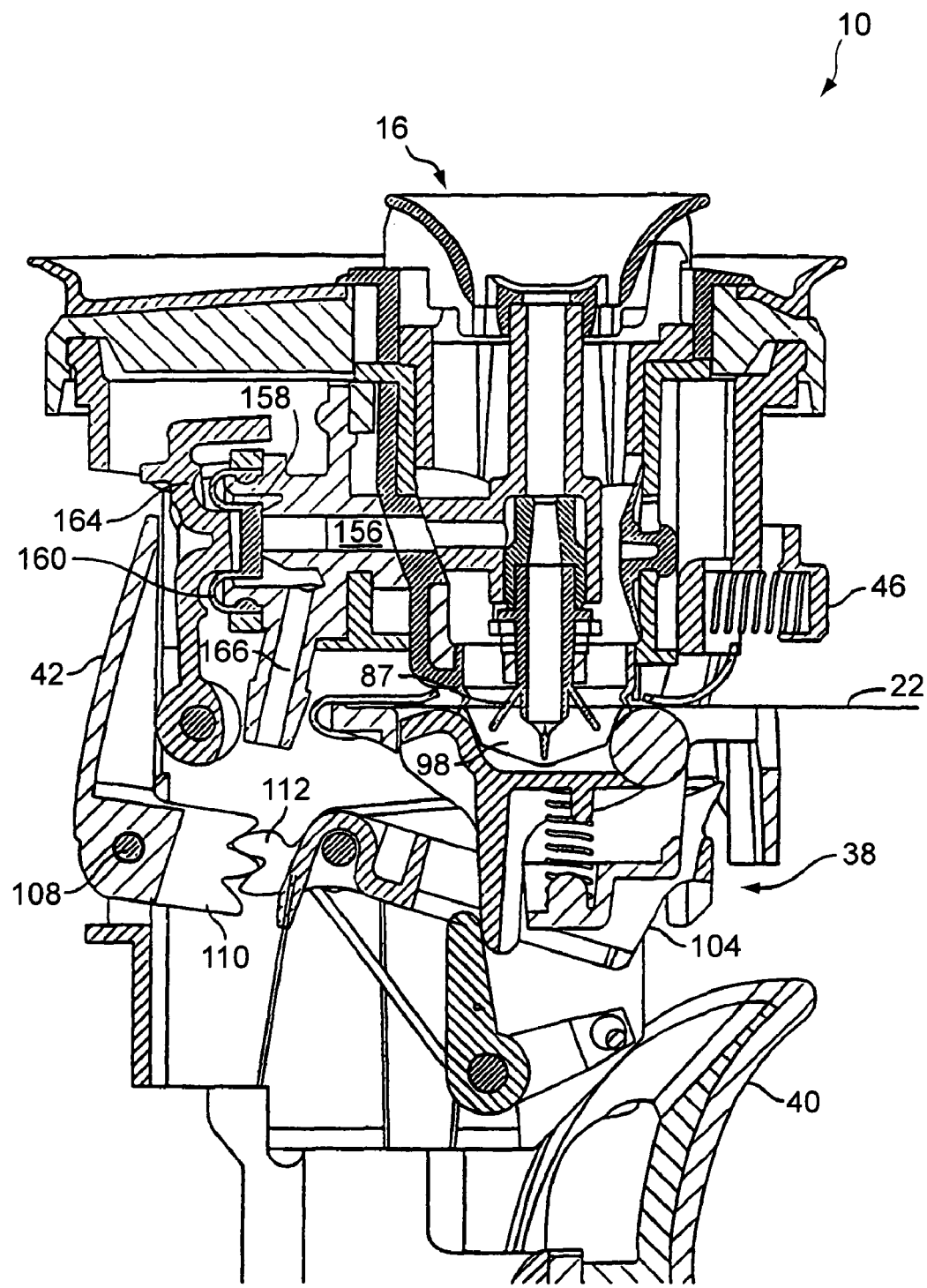

As illustrated in FIG. 10L, when fire button 42 is pushed, gear teeth 110 are pivoted about pivot pin 108, causing lifter 104 of carriage assembly 38 to move receptacle 22 toward aerosolization mechanism 16. When fully depressed, pointed tip 50 and side punches 80 pierce through receptacle 22 and enter into pocket 98 as shown. Stop 86 engages carriage assembly 38 (see FIG. 10N) to ensure that pointed tip 50 and side punches 80 are not pressed through the bottom of pocket 98 while seal 87 provides a seal between aerosolization mechanism 16 and receptacle 22. Depression of fire button 42 causes valve actuator 164 of actuator arm 138 to be released from its over-center position, thereby unlocking valve 132. The high pressurized gas stored within base unit 12 then flows through lumen 166 as shown by the arrow, causing valve 132 to "pop open." More specifically, the release of valve actuator 164 causes the high pressurized gas to come into contact with the underside of diaphragm 160 causing valve seat 158 to be lifted from passage 156. In this manner, air is allowed to flow through passage 156 and into aerosolization mechanism 16. The high pressurized gas then extracts the powdered medicament from pocket 98, deagglomerates the powdered medicament and disperses the powdered medicament into the capture chamber as previously described.

One particular advantage of aerosolization apparatus 10 is that the powdered medicament is extracted from receptacle 22 almost immediately after it has been pierced by aerosolization mechanism 16. In this manner, the powdered medicament within receptacle 22 remains fresh until it is aerosolized.

Figure 10M:
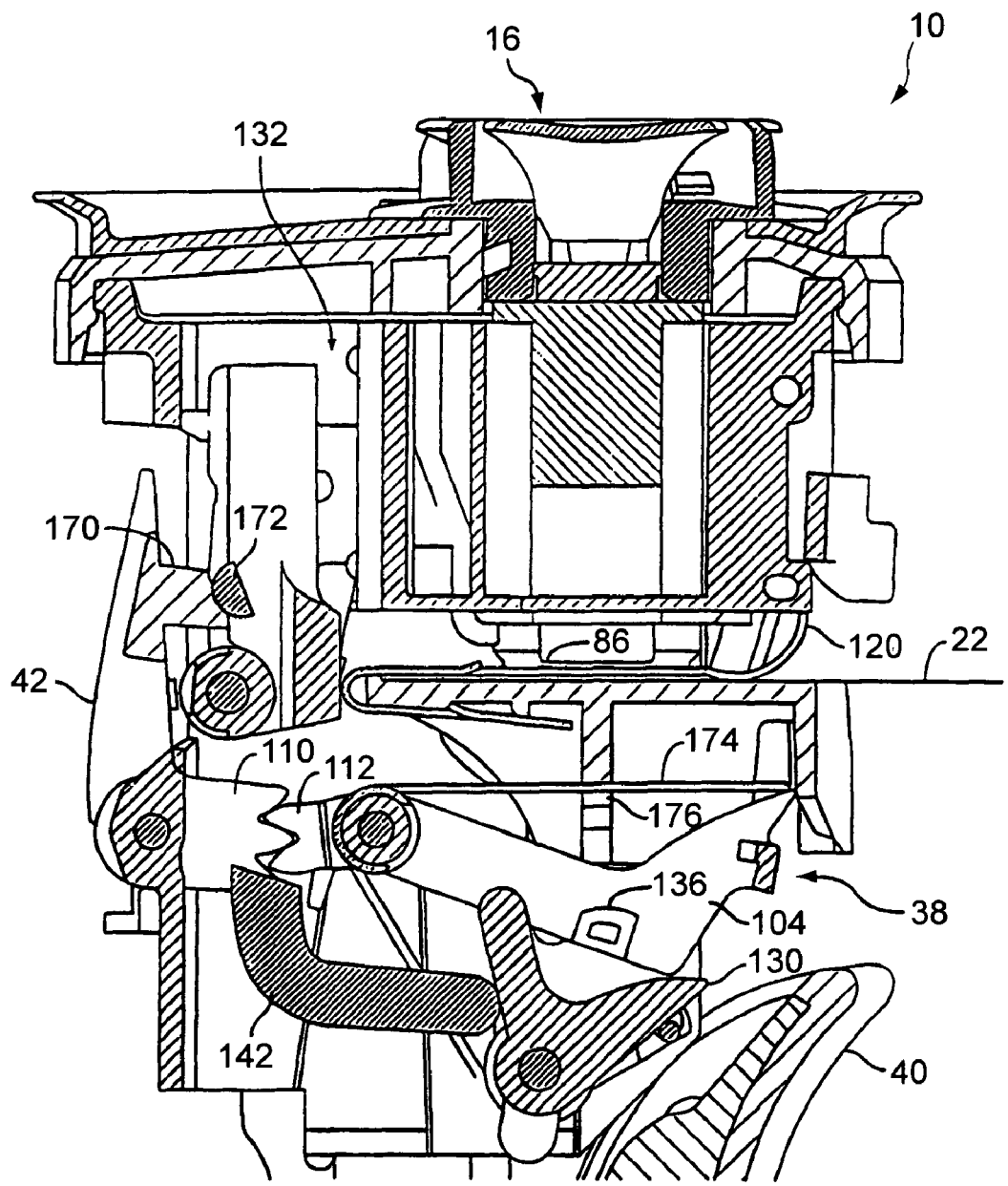
Figure 10N:
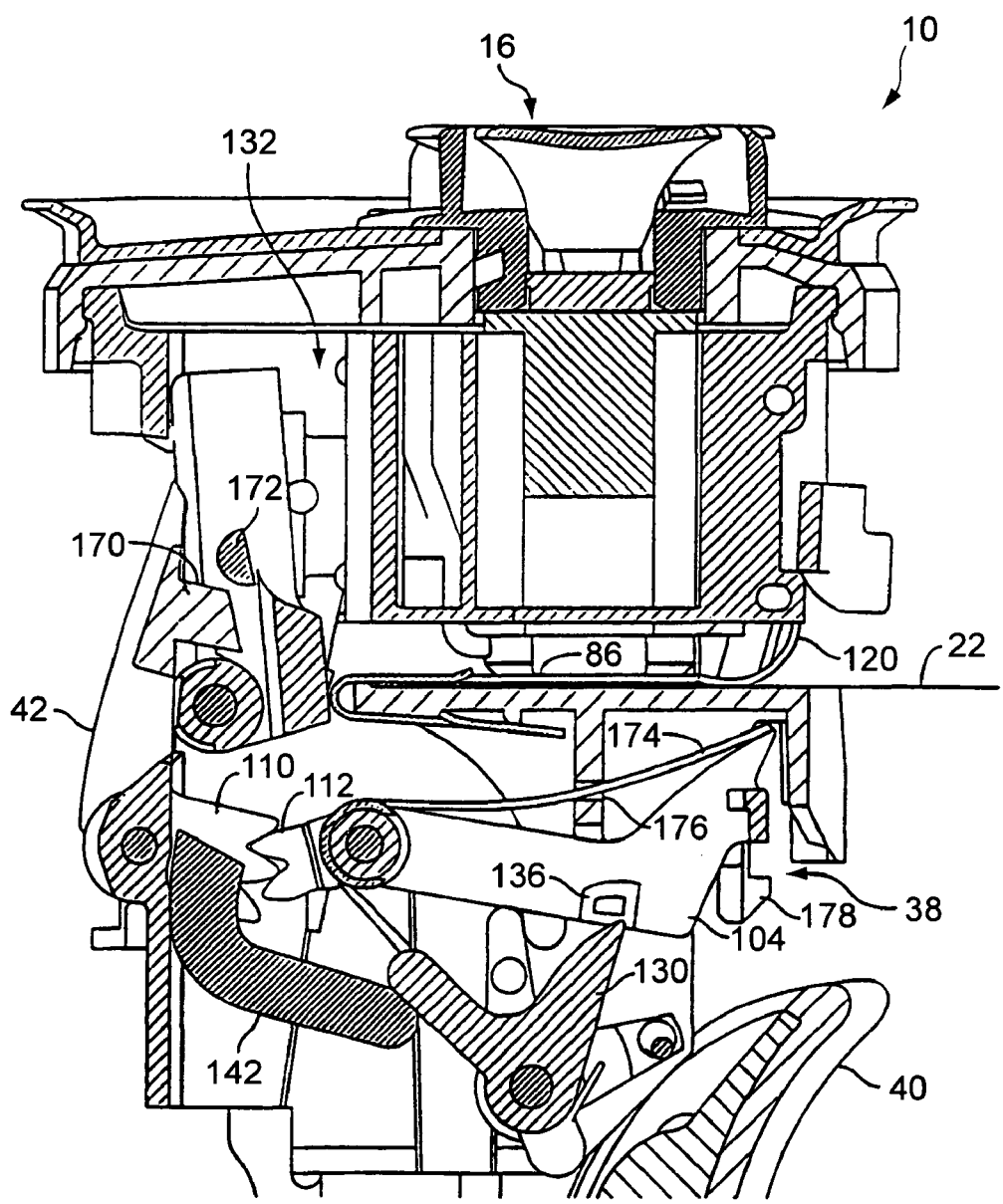

Referring now to FIGS. 10M and 10N, operation of fire button 42 to release actuator arm 138 from the locked position will be described. Fire button 42 includes a tab 170 which engages a post 172 on valve set arm 142. As fire button 42 is further depressed, tab 170 pushes valve set arm 142 out from under boss 152 on chassis 150 (see FIG. 10H). In turn, valve actuator arm 138 is allowed to move back away from its over-center position, unclamping diaphragm 160 (see FIG. 10L). As illustrated in FIG. 10N, fire button 42 is fully depressed so that post 172 on set arm 142 is in a released position.

Still referring to FIGS. 10M and 10N, as fire button 42 is pressed, gear teeth 110 and 112 operate to transfer trigger motion from fire button 42 to lifter 104. A spring beam 174 is included on lifer 104 and engages a notch 176 in carriage assembly 38. Spring beam 174 is employed to raise carriage assembly 38 so that receptacle 22 may be coupled to aerosolization mechanism 16. As illustrated in FIG. 10M, stop 86 on aerosolization mechanism 16 has not quite come into contact with carriage assembly 38. In FIG. 10N, carriage assembly has engaged stop 86 to stop motion of carriage assembly 38. Further, spring beam 174 is deformed due to the further upward travel of lifter 104. In this way, spring beam 174 will serve to lower carriage assembly 38 back to the starting position after inhalation is complete as described hereinafter.

Figure 10O:
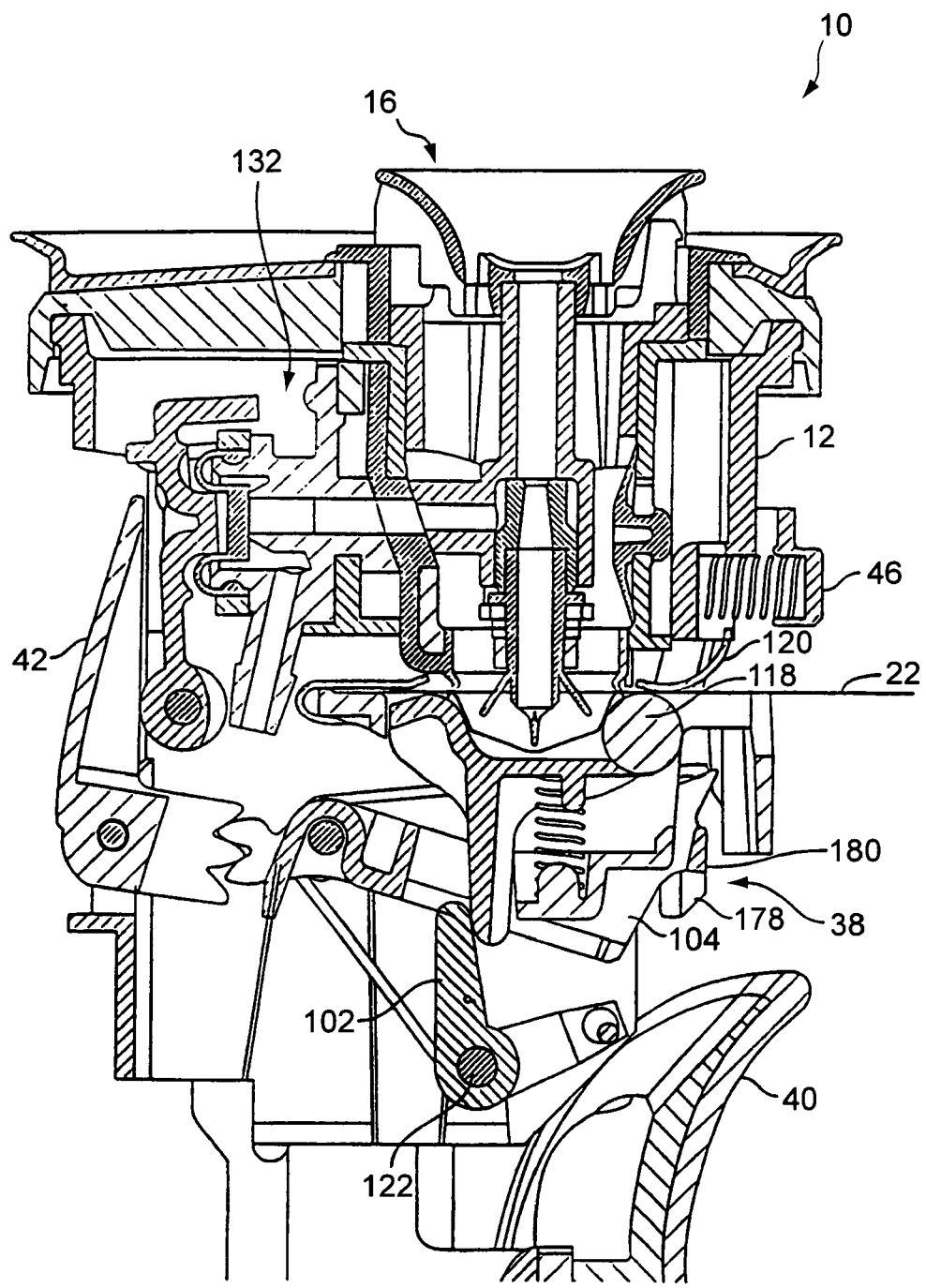
Figure 10P:
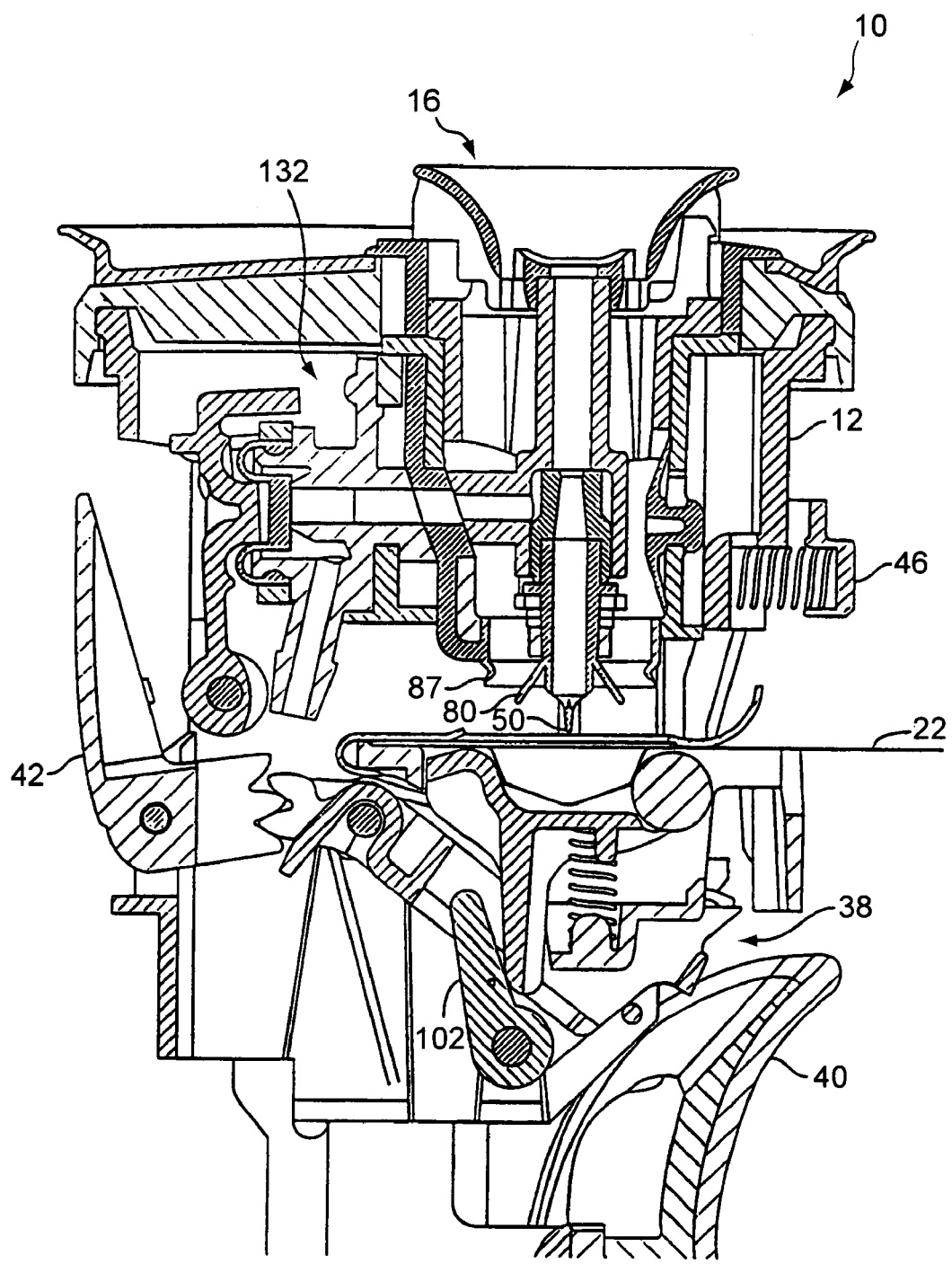

Base unit 12 includes a hook 178 which is coupled to release button 46 (see FIG. 10L). Hook 178 catches a tab 180 on lifter 104 when carriage assembly 38 is fully raised and the pressurized gas has been released as illustrated in FIG. 10O. When release button 46 is pressed, hook 178 is released from tab 180 so that carriage assembly 38 may be lowered to the starting position. As previously described, spring beam 174 assists in moving carriage assembly 38 back to the starting position. As shown in FIG. 10P, carriage assembly 38 has been returned to the starting or ready position where receptacle 22 may be removed by pulling it from carriage assembly 38.

One particular advantage of employing release button 46 is that aerosolization mechanism 16 remains coupled to receptacle 22 until fire button 42 is pressed. In this way, a user is prevented from piercing a receptacle and then lowering carriage assembly 38 without aerosolizing the medicament.

Figure 11:
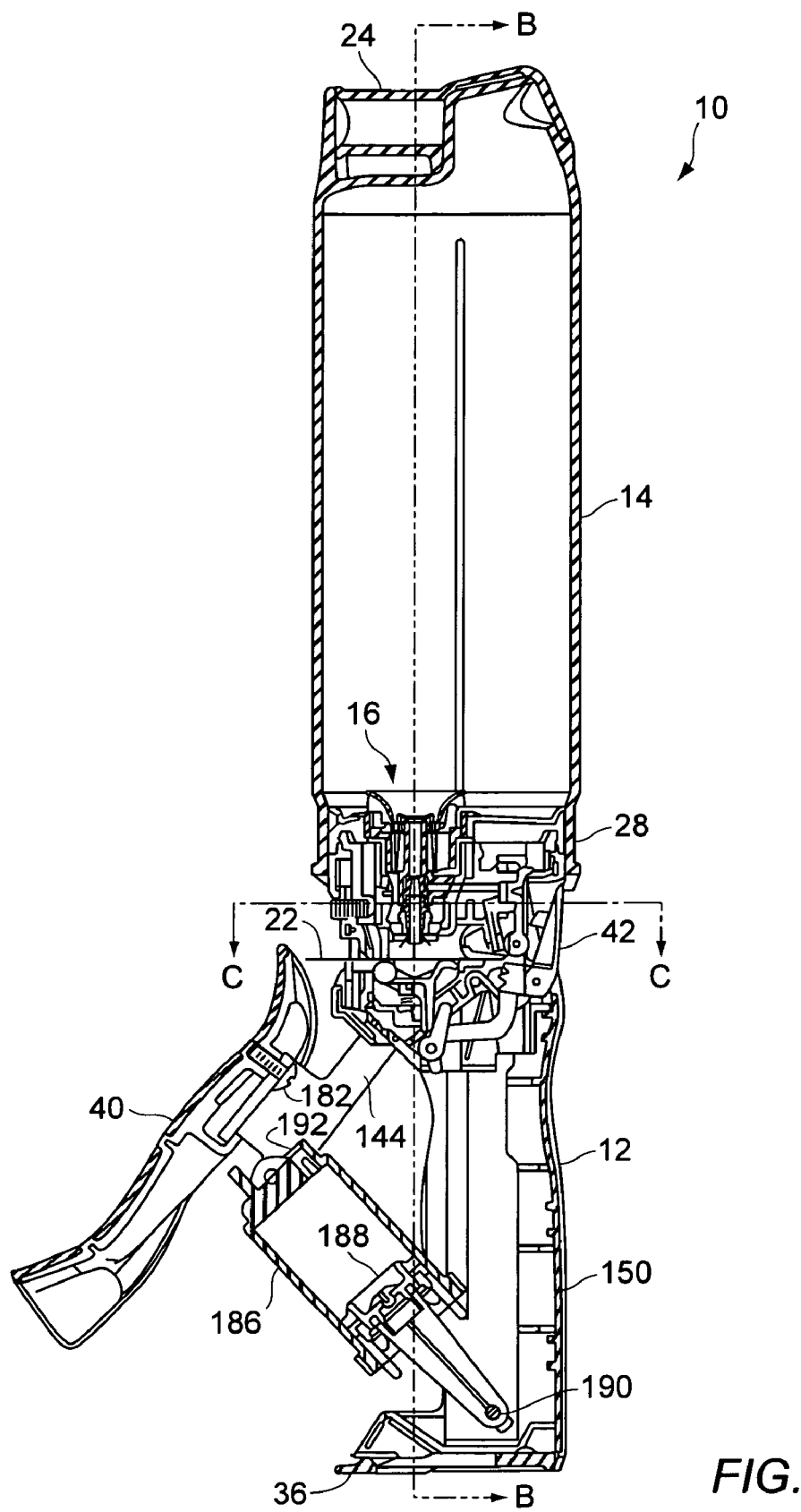
FIG. 11 is a cross-sectional side view of the aerosolization apparatus of FIG. 1 showing the handle extended to pressurize a gas within a cylinder according to the invention.
Figure 11A:
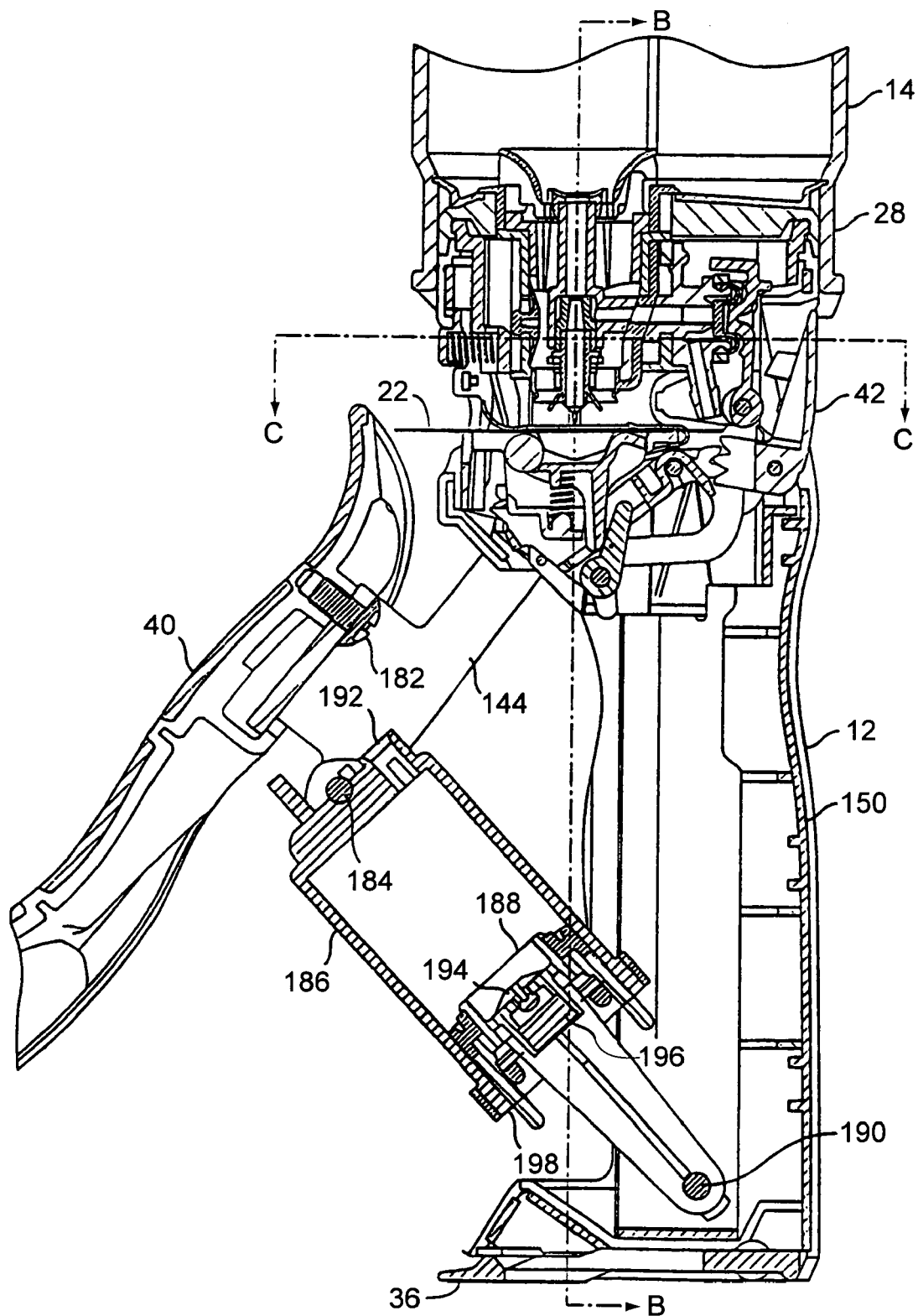
FIG. 11A illustrates a magnified view of the base of the aerosolization apparatus of FIG. 11.
Figure 11B:
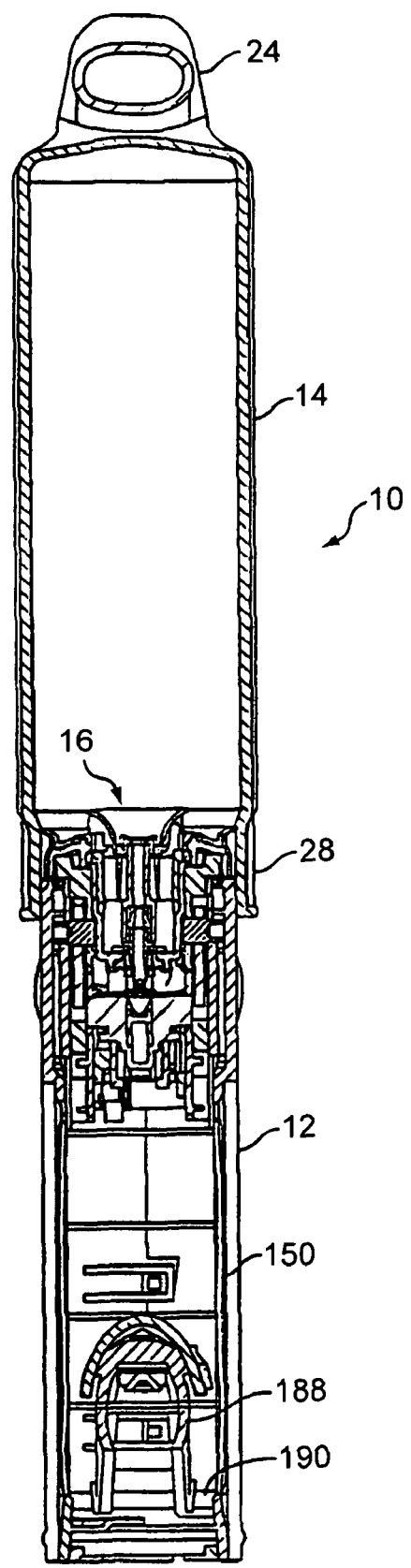
FIG. 11B is a cross-sectional side view of the apparatus of FIG. 11 taken along lines B-B.
Figure 11C:
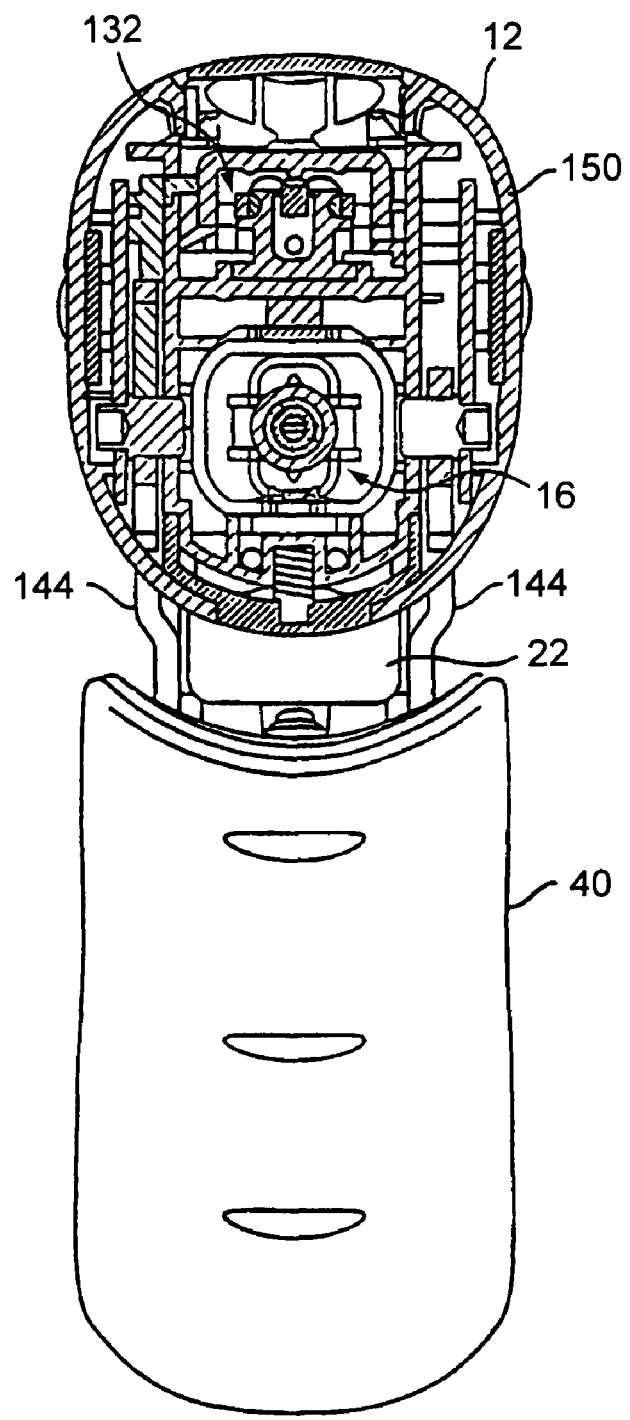
FIG. 11C is a cross-sectional top view of the aerosolization apparatus of FIG. 11 taken along the lines C-C.
Figure 12:
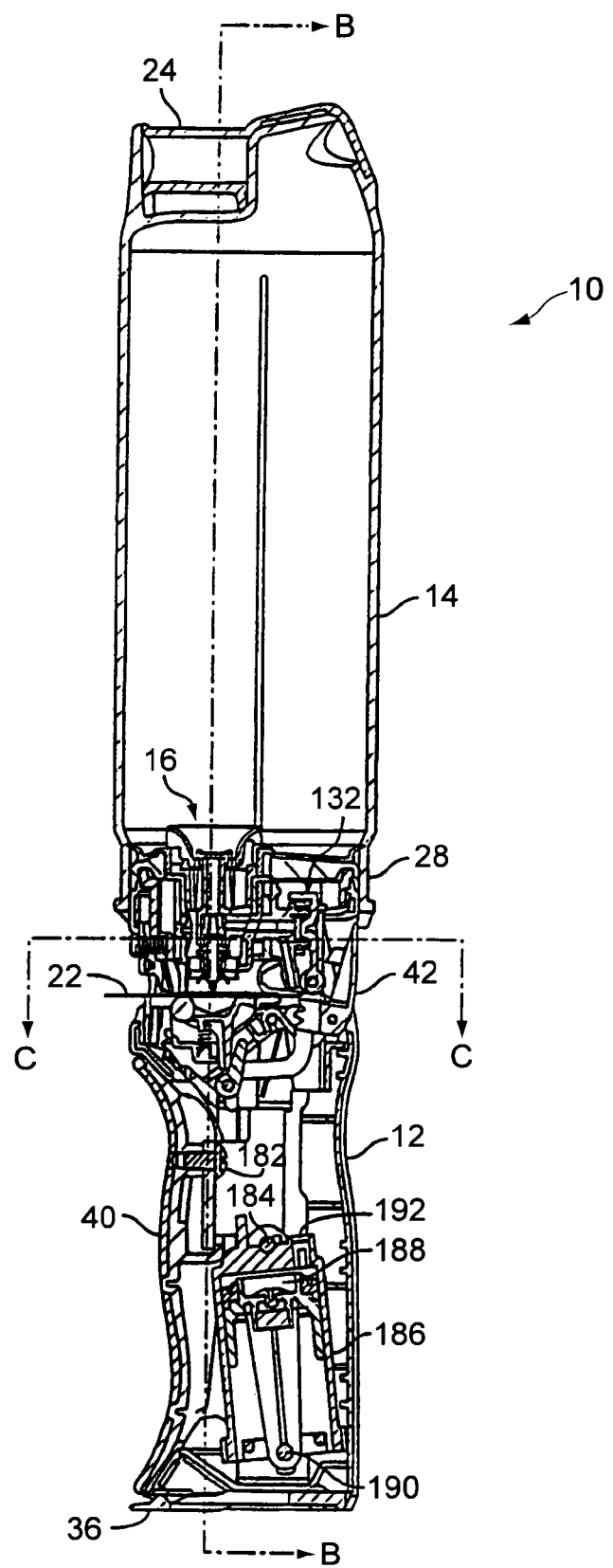
FIG. 12 is a cross-sectional side view of the aerosolization apparatus of FIG. 1 showing the handle in a home or retracted position after the pressurized gas has been produced within the cylinder according to the invention.
Figure 12A:
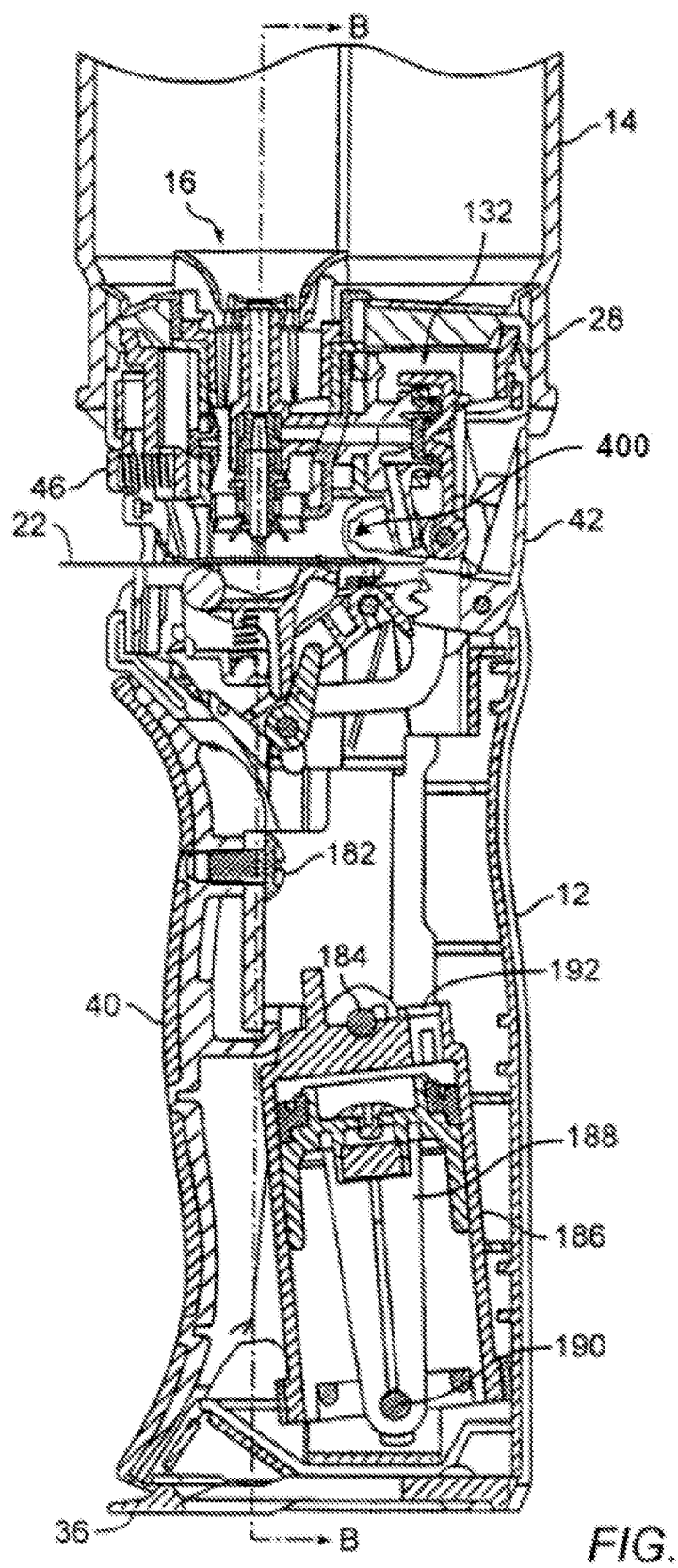
FIG. 12A illustrates a magnified view of the base of the aerosolization apparatus of FIG. 11.
Figure 12B:
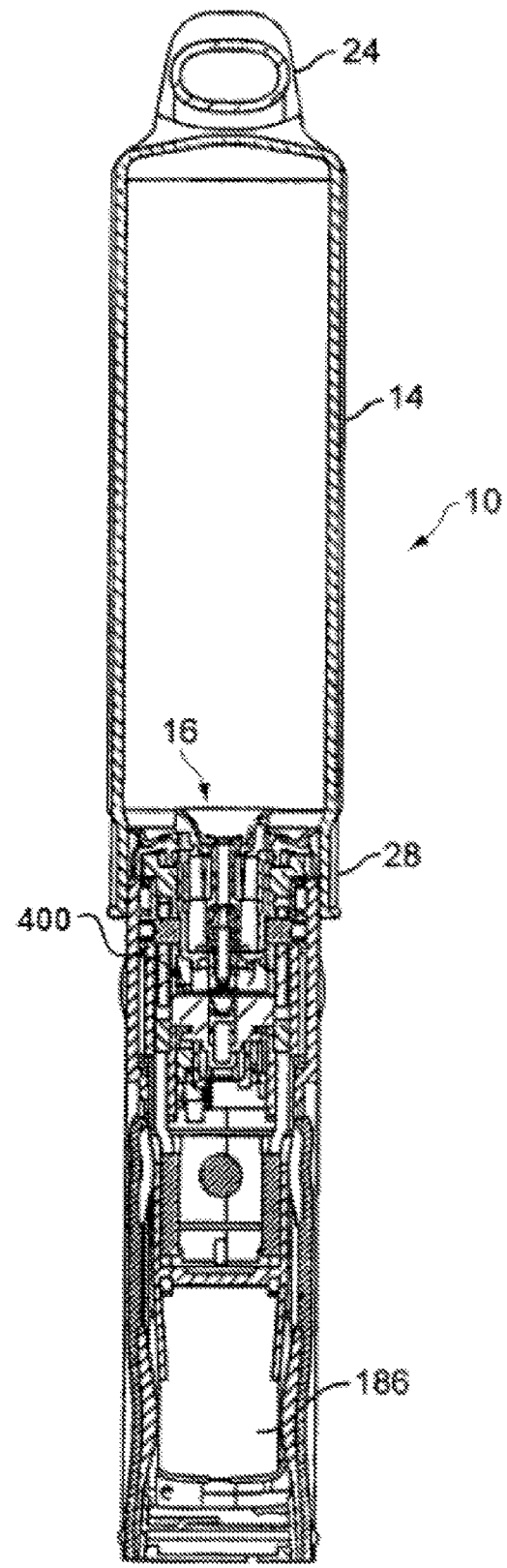
FIG. 12B is a cross-sectional side view of the apparatus of FIG. 12 taken along lines B-B.
Figure 12C:
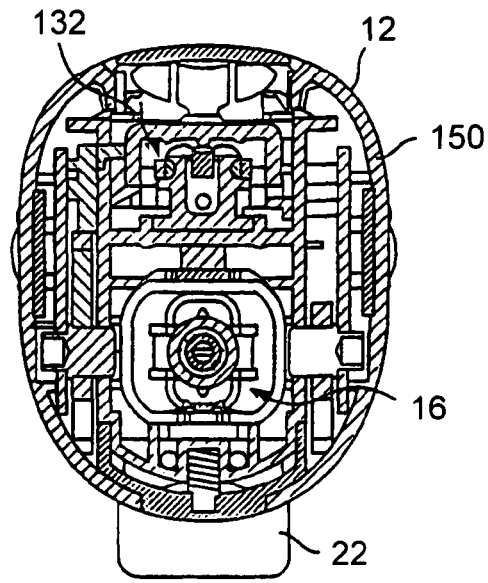
FIG. 12C is a cross-sectional top view of the aerosolization apparatus of FIG. 12 taken along the lines C-C.

Referring now to FIGS. 11-11B and 12-12B, operation of handle 40 to produce a pressurized gas for delivery aerosolization mechanism 16 will be described. Handle 40 is coupled to pump link 144 via a screw 182. Pump link 144 is further coupled by a pivot pin 184 to a cylinder 186. A piston 188 is pivotally attached by a pivot pin 190 to chassis 150 of base unit 12. Piston 188 is slidable within cylinder 186 to produce a pressurized gas. Cylinder 186 further includes an opening 192 to which a tube (not shown) is connected. The tube extends through base unit 12 and is coupled to fitting 168 to hydraulically couple cylinder 186 with valve 132 if valve 132 is not in the locked position, translation of piston 188 within cylinder 186 causes diaphragm 160 to flex, thereby allowing air to pass through valve 132 as previously described. If, however, valve 132 is locked, translation of piston 188 within cylinder 186 produces a pressurized charge of gas within cylinder 186. In FIGS. 11-11B, handle 40 has not quite reached the fully extended position. As such, valve actuator 164 is not yet in the locked position. In FIGS. 12-12B, handle 40 has been extended to the fully extended position to lock valve actuator 164 of actuator arm 138 and then moved back to the home position. As such, a pressurized gas exists within cylinder 186 and is ready for delivery to aerosolization mechanism 16 upon operation of fire button 42 as previously described.

As best shown in FIG. 11A, use of pivot pins 184 and 190 allows cylinder 186 to remain generally aligned with piston 188 during extension and retraction of handle 40. As such, the amount of wear between cylinder 186 and piston 188 is greatly reduced. Further, maintaining proper alignment between cylinder 186 and piston 188 reduces the amount of force required to move handle 40 when pressurizing the gas. For example, when cylinder 186 has a volume of approximately 8 ml at the fully extended position, a force of approximately ten pounds will be required to move handle 40 back to the home position and pressurize the gas. Maintaining piston 188 generally aligned with cylinder 186 during operation of handle also allows a generally constant or smooth force to be employed when operating handle 40.

Still referring to FIG. 11A, piston 188 includes a check valve 194 and filter 196. Check valve 194 is configured so that, as handle 40 is extended, air is allowed to enter into cylinder 186 through check valve 194. When handle 40 is moved back to the home position, check valve 194 closes so that the pressurized gas may be produced within cylinder 186. Filter 196 is provided to filter the air entering into cylinder 186. Errant powder from previous operations may fall into bottom of base unit 12. Filter 196 prevents such powder from entering into cylinder 186. To further assist in preventing errant powder from entering into cylinder 186, cylinder 186 is mounted such that an open end 198 of cylinder 186 is pointed generally downward. In this way, errant powder falling through base unit 12 will not fall directly onto piston 188 where it may tend to be drawn into cylinder 186 during operation.

Figure 13:
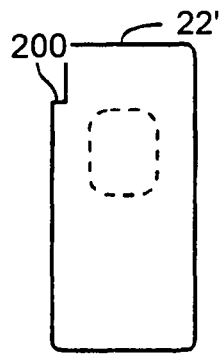
FIG. 13 illustrates a top view of one embodiment of a receptacle having a keyed notch to regulate insertion of the receptacle into an aerosolization apparatus according to the invention.
Figure 14:
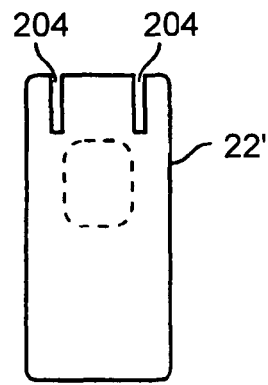
FIG. 14 illustrates another alternative embodiment of a receptacle having a pair of keyed notches according to the invention.

As previously described, if receptacle 22 is not fully inserted into carriage assembly 38, fire button 42 may not be operated to couple receptacle 22 to aerosolization mechanism 16. Hence, receptacles used with aerosolization apparatus 10 may be keyed to prevent complete insertion of the receptacle into carriage assembly 38 unless the proper receptacle is being inserted. In this way, the receptacles may be keyed according to the powdered medicament they contain so that a patient will not receive an improper medication. An exemplary scheme for keying the receptacles is illustrated in FIGS. 13 and 14. In FIG. 13, a receptacle 22' includes a notch 200. Receptacle 22' is used with an aerosolization apparatus where the carriage assembly includes a key (such as key 400 shown in FIGS. 12A and 12B, in one approach) which is received within notch 200 when receptacle 22' is inserted into the carriage assembly. If the receptacle does not include notch 200, the receptacle may not be fully inserted, thereby preventing operation of the carriage assembly as previously described. As illustrated in FIG. 14, a receptacle 22" includes a pair of notches 202 and 204. With such a configuration, the carriage assembly will include a pair of keys (which are not shown in the figures) that are aligned with notches 202 and 204 to allow receptacle 22" to be fully inserted. By increasing the number and placement of the various notches and keys, a wide variety of combinations may be produced so that receptacles with a wide assortment of drugs may be keyed to particular aerosolization apparatus to prevent incorrect delivery to a patient. Although shown with rectangular notches, it will be appreciated that any geometry of notch or indentation may be employed as long as full insertion of the receptacle is prevented unless the receptacle is intended for a particular aerosolization apparatus.

The foregoing invention has now been described in detail by way of illustration and example, for purposes of clarity of understanding. However, it will be appreciated that certain changes and modifications may be practiced within the scope of the dependent claims.

What is claimed is:

1. A system, comprising:

a receptacle comprising at least one notch and a cavity that holds medicament; and a device comprising:

a housing, the housing having an opening that receives and supports the receptacle;

an extraction tube that engages the receptacle;

at least one piercing element that cuts the receptacle to create at least one opening in a wall of the receptacle;

a first and a second interlock which are operably engageable with a carriage assembly to prevent coupling of the receptacle with the extraction tube; and at least one key that mates with the at least one notch of the receptacle, wherein when the receptacle is inserted into the opening that receives the receptacle and the at least one key mates with the at least one notch of the receptacle, the at least one piercing element is allowed to cut the receptacle, wherein when the receptacle is partially inserted into the opening that receives the receptacle and the at least one key does not mate with the at least one notch of the receptacle, the at least one piercing element is prevented from cutting the receptacle, wherein the first interlock is released to allow movement of the carriage upon movement of a handle to an extended position, and wherein the second interlock is engaged when the receptacle is partially inserted into the carriage assembly.

2. The system of claim 1, wherein the at least one notch of the receptacle comprises two notches.

3. The system of claim 1, wherein the at least one piercing element comprises a plurality of piercing elements that cut a plurality of holes in the receptacle.

4. The system of claim 1, wherein when the receptacle is inserted into the opening that receives the receptacle and the at least one key mates with the at least one notch of the receptacle, the cavity of the receptacle is aligned with the at least one piercing element.

5. The system of claim 1, wherein when the receptacle is inserted into the opening that receives the receptacle and the at least one key mates with the at least one notch of the receptacle, the extraction tube is allowed to engage the receptacle.

6. The system of claim 1, wherein when the receptacle is partially inserted into the opening that receives the receptacle and the at least one key does not mate with the at least one notch, the extraction tube is prevented from engaging the receptacle.

7. The system of claim 1, wherein when the receptacle is inserted into the opening that receives the receptacle and the at least one key mates with the at least one notch of the receptacle, a portion of the receptacle remains outside the device.

8. The system of claim 1, wherein the device further comprises a well that receives the receptacle.

9. The system of claim 1, wherein the device further comprises a deagglomeration channel in communication with the extraction tube.

10. The system of claim 1, wherein the device further comprises a check valve that opens when a patient inhales at a threshold pressure.

11. The system of claim 1, wherein the at least one opening is an air inlet opening.

12. The system of claim 1, wherein the receptacle comprises a powder-containing receptacle, wherein the extraction tube is structured and arranged to deliver the powder from the receptacle to an outlet, and wherein the piercing element is configured to create at least one opening in the wall of the receptacle by causing a puncture in the wall and causing a tearing of the wall.

13. The system of claim 1, wherein the device further comprises a carriage assembly adapted to receive the receptacle and to couple the receptacle to the extraction tube.

14. The system of claim 13, wherein the device further comprises a fire button that is connected to the carriage assembly to move the carriage assembly toward the extraction tube.

15. The system of claim 1, wherein the device further comprises a capture chamber.

16. The system of claim 1, wherein the at least one notch of the receptacle comprises two notches, and wherein the at least one piercing element comprises a plurality of piercing elements that cut a plurality of holes in the receptacle.

17. The system of claim 1, wherein when the receptacle is inserted into the opening that receives the receptacle and the at least one key mates with the at least one notch of the receptacle, the cavity of the receptacle is aligned with the at least one piercing element, and wherein the at least one piercing element comprises a plurality of piercing elements that cut a plurality of holes in the receptacle.

18. The system of claim 1, wherein the device further comprises a deagglomeration channel in communication with the extraction tube, and wherein the at least one piercing element comprises a plurality of piercing elements that cut a plurality of holes in the receptacle.

19. The system of claim 1, wherein the device further comprises a check valve that opens when a patient inhales at a threshold pressure, and wherein the at least one piercing element comprises a plurality of piercing elements that cut a plurality of holes in the receptacle.

* * * * *